US008064568B2

United States Patent
Von Der Haar

(10) Patent No.: US 8,064,568 B2
(45) Date of Patent: Nov. 22, 2011

(54) METHOD AND DEVICE TO GENERATE PROJECTIONS OF THE INSIDE OF AN EXAMINATION SUBJECT

(75) Inventor: Thomas Von Der Haar, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/755,505

(22) Filed: Apr. 7, 2010

(65) Prior Publication Data

US 2010/0254508 A1 Oct. 7, 2010

(30) Foreign Application Priority Data

Apr. 7, 2009 (DE) .......................... 10 2009 016 770

(51) Int. Cl.
*A61B 6/00* (2006.01)

(52) U.S. Cl. .............................. 378/9; 378/147; 378/150

(58) Field of Classification Search .............. 378/9, 147, 378/150
See application file for complete search history.

(56) References Cited

U.S. PATENT DOCUMENTS

| | | | | |
|---|---|---|---|---|
| 4,150,293 A | * | 4/1979 | Franke | 378/9 |
| 4,200,799 A | * | 4/1980 | Saito | 378/13 |
| 4,998,268 A | * | 3/1991 | Winter | 378/63 |
| 5,966,422 A | * | 10/1999 | Dafni et al. | 378/9 |
| 6,320,929 B1 | | 11/2001 | Von Der Haar | |
| 6,445,761 B1 | | 9/2002 | Miyazaki et al. | |
| 6,501,828 B1 | | 12/2002 | Popescu | |
| 7,194,061 B2 | * | 3/2007 | Fujita | 378/9 |
| 7,583,782 B2 | * | 9/2009 | Yamazaki | 378/4 |
| 7,920,670 B2 | * | 4/2011 | Hugg et al. | 378/4 |
| 2004/0008810 A1 | * | 1/2004 | Nelson et al. | 378/19 |
| 2005/0089134 A1 | | 4/2005 | Bruder et al. | |
| 2005/0111623 A1 | * | 5/2005 | Bruder et al. | 378/95 |
| 2005/0169431 A1 | * | 8/2005 | Groh et al. | 378/150 |
| 2006/0177002 A1 | * | 8/2006 | Toth et al. | 378/150 |
| 2007/0086576 A1 | * | 4/2007 | Yang | 378/152 |
| 2008/0075225 A1 | * | 3/2008 | Kalender | 378/20 |
| 2008/0317212 A1 | * | 12/2008 | Kuehn et al. | 378/151 |

FOREIGN PATENT DOCUMENTS

WO  WO 2009/083850  7/2009

OTHER PUBLICATIONS

Abstract of FR 27 00259 A1.
"Einführung in die Computertomographie," Buzug (2004) pp. 209-217.

* cited by examiner

*Primary Examiner* — Edward Glick
*Assistant Examiner* — Alexander H Taningco
(74) *Attorney, Agent, or Firm* — Schiff Hardin LLP

(57) ABSTRACT

In a radioscopic method and device to generate projections of the inside of an examination subject that is located in an examination space of a data acquisition unit, a number of ray beams are generated that are directed toward the examination space and that each exhibit a fan angle in a rotation plane. The number of ray beams are rotated in the rotation plane in a rotation direction the examination space, while the fan angle is varied during the rotation.

13 Claims, 23 Drawing Sheets

METHOD AND DEVICE TO GENERATE PROJECTIONS OF THE INSIDE OF AN EXAMINATION SUBJECT

BACKGROUND OF THE INVENTION

1. Field of the Invention

The present invention concerns a method to generate projection images of the inside of an examination subject. The invention furthermore concerns a device to generate projection images of the inside of an examination subject and a control device for such a device.

2. Description of the Prior Art

A method of the general type described above is typically applied in a computed tomography device (CT device). Such a CT device 1 is shown in FIG. 1. Volume exposures and/or slice images of the inside of an examination subject 2 can be generated in a non-invasive manner with the CT device 1. In order to enable a complete reconstruction of the three-dimensional anatomy of the examination subject 2, projections (projection data sets) $P_i$ of the examination subject 2 must initially be made from different viewing directions. The spatial exposures and/or slice images are then reconstructed from the projections $P_i$.

For the acquisition of the projections $P_i$, the examination subject 2 is positioned in an examination space 3 and an x-ray source 4 and a detector system 5 are rotated around the examination subject 2 in a rotation direction R. The detector system 5 is arranged diametrical to the rotation center relative to the x-ray source 4, so the rotation center coincides with the center of the examination space 3. The detector system 5 has a number of discrete detectors distributed circumferentially with alignment on the x-ray source 4. These detectors are known as channels $6_i$ to those skilled in the art.

The x-ray source 4 serves to generate the x-rays. A diaphragm device 7 (the position of which is indicated only schematically in FIG. 1) is located between the focus 10 of the x-rays and the examination subject 2 at the x-ray source 4. With the diaphragm device 7, the x-rays are delimited in the form of a ray beam 8, for example in the form of a fan or cone beam. The diaphragm device 7 is most often realized as a slit diaphragm and, by its slit dimensions, demarcates a fan angle $\theta$ of the ray beam 8, with the x-ray radiation that strikes the slit diaphragm outside of the slit dimension being masked (absorbed). In order to optimally acquire data for the entire examination subject 2 with each projection $P_i$, the fan angle $\theta$ must be made relatively large; a value of 50° is typical for normal whole body exposures, for example. The circumferential extent of the detector system 5 is also accordingly large, with the individual channels $6_i$ being located at discrete positions along this circumferential extent, as is schematically indicated in FIG. 1. The same essentially also applies in the use of detectors known as multi-line detectors, in which multiple lines of channels $6_i$ arranged adjacent to one another are fashioned transverse to the circumferential dimension, i.e. parallel to the rotation axis of the system. The ray beam—in the present case a conical fan or cone beam—is then dimensioned such that these adjacent lines are struck by x-rays attenuated y the subject 2 as well.

In order to be able to meaningful reasonable images, projection data from all directions should be present for each channel $6i$. It should be noted that consideration of an examination subject from opposite directions delivers no additional information. Therefore, the combination of the x-ray source 4, the diaphragm device 7 and the detector system 5 that is mounted on a gantry 9 must be rotated by at least 180°, plus the fan angle $\theta$ of approximately 50° plus a transition angle of approximately 30°. Even though the minimum total angle necessary for the image reconstruction therefore amounts to approximately 260°, this "partial revolution", as it is called, is designated as a "180° scan". This situation is schematically depicted in FIG. 2, wherein not the full rotation of the stated 260°, but rather only a segment of this that is necessary for further explanation of the function, is shown. Located in the circumferential direction is a focus 10 of the ray beam 8 (ray beam 8 represented with solid lines), initially at the position of approximately $\phi = -25°$ (ray beam 8 represented with broken lines). The known diaphragm used to delimit the ray beam 8 has a diaphragm aperture 1 that is independent of the rotation angle $\phi$. In addition to a number of functions, among other things the operation of the x-ray source 4 and the rotation of the gantry 9 are controlled by a control device 32 (shown in FIG. 1) that for this purpose has an x-ray source control module 32A and a gantry control module 32B.

A contribution of the individual channels $6_i$ for the reconstruction of images of the inside of the examination subject 2—and therefore also their suitability for use in this reconstruction—is illustrated in FIG. 3 in the form of a sinogram. The channels $6_i$ through $6_n$ (generally $6_i$) are plotted on the x-axis and the projections $P_i$ are plotted on the y-axis, for example in time intervals of 1 ms during the rotation. The upper triangular region 12 and the lower triangular region 13 cannot be used for the reconstruction because not all channels $6i$ deliver a contribution at those regions. Only the rectangular region 14 is usable for reconstruction.

It should be noted that the examination subject 2 is continuously exposed while the gantry 9 rotates, but only a portion of the applied dose can actually be used for image reconstruction. The unusable dose is predominantly applied at the beginning and end of the partial revolution, as is apparent from FIG. 3. The proportion of the unused dose increases with the size of the fan angle $\theta$ and decreases with increasing rotation angle $\phi$. The relative proportion of the unused dose is calculated as the quotient of the fan angle $\theta$ and the rotation angle $\phi$. The effect is greatest in the 180° scan and amounts to approximately 19% of the total dose.

This disadvantage exists only for the single source CT device 1 but also described above, in a further type of device known as a dual source CT device, in which two ray beams 8 are used that are offset by 90° from one another. The two ray beams are rotated by 90°. Such a partial revolution is accordingly also designated as a 90° scan. The sinogram of such a dual source CT device is shown in FIG. 23. The aforesaid triangle regions 12 and 13 that cannot be used for reconstruction exist in this case as well. In contrast to the sinogram of the single source CT device 1, however, three usable rectangular regions 14 now exist between these outer triangular regions 12 and 13, with the middle rectangular region 14 being acquired by contributions of the two ray beams 8 that supplement one another.

In summary, with regard to the unusable triangular regions 12 and 13 it should be noted that it is desirable (in particular for medical applications) to keep the dose as low as possible in order to expose the examination subject to an optimally low radiation dose.

SUMMARY OF THE INVENTION

An object of the present invention is to provide a method and a device of the aforementioned type so that the proportion of the unused dose is reduced as much as possible.

According to the invention, in a radioscopic method to generate projections of the inside of an examination subject (that is located in an examination space) includes the steps of:

generating a number of ray beams that are directed toward the examination space and that each exhibit a fan angle in a rotation plane, and rotating the number of ray beams in the rotation plane in a rotation direction around the examination space, while varying the fan angle during the rotation.

A device according to the invention for the generation of projections of the inside of an examination subject arranged in an examination space has a number of radiation sources that each generate an x-ray beam, so a number of ray beams are generated. Each ray beam exhibits a fan-shaped expansion in a rotation plane in the circumferential direction around the examination space. Such a ray beam is therefore designated as a fan beam. Cone beams are also typical that in turn exhibit a fan-shaped structure of interest in the present context, but in the circumferential direction. Therefore cone beams are also encompassed by the terms "fan beam" or "ray beams that exhibit a fan angle".

Furthermore, the device has a number of diaphragm devices that are each fashioned to delimit and to vary the fan angle of one of the ray beams, and a detector system that is fashioned to detect the projections generated by a ray beam. The device furthermore has a gantry that is fashioned to rotate the number of radiation sources and the number of diaphragm devices by a rotation angle in the rotation direction around the examination space, and a control device to activate the number of radiation sources and/or the diaphragm devices.

The detector system can be a stationary (non-rotatable) ring detector. However, since such ring detectors are relatively expensive, a number of discrete detector systems can also be used, these detector systems being mounted to the gantry in a distribution in the circumferential direction, and therefore are rotated as well synchronously with the number of radiation sources or x-ray sources.

The control device is fashioned according to the invention to control the size of the fan angle depending on the rotation position (i.e. the current rotation angle) of the radiation sources in the rotation plane around the examination space.

The method and control according to the invention allow only that region of the examination subject from which projections are actually used for image reconstruction to be selectively exposed in a partial revolution. This enables a significant dose reduction. Depending on the number of radiation sources provided, a 180° scan or a 90° scan can be implemented. Given availability of a single x-ray source a 180° scan is thus implemented, in contrast to which a 90° scan can also be implemented given availability of two x-ray sources.

In an embodiment of the invention, given a rotation by a predetermined rotation angle, the value of the fan angle can be increased from a start value to an end value in an initial range of the rotation angle, and the value of the fan angle can be reduced from the end value down to the start value in an end range of the rotation angle. A value of 0°, which amounts to a closed diaphragm, is typically used as a start value. Any value at which the desired exposure or irradiation of the examination subject and/or of the opposite detector is ensured is typically used as an end value. Given adjacent diaphragms placed in the beam path direction, this end value can be, for example, the angle produced by the maximum achievable width of the diaphragm aperture of a movable diaphragm element that is moved adjacent to a fixed diaphragm element. When two jaw-like diaphragm elements that are adjacent in the circumferential direction are used, and a diaphragm with a fixed diaphragm aperture is omitted entirely, the end value can even be variably adjusted depending on the respective application case.

According to a preferred embodiment of the invention, the increase of the value of the fan angle ensues by a—continuously or quasi-continuously, step-by-step—blending in of rays of the ray beam from a border region of the ray beam situated opposite to the rotation direction toward a border region of the ray beam situated in the rotation direction. Moreover, in this embodiment, the decrease of the value of the fan angle ensues by a—continuously or quasi-continuously, step-by-step—masking of rays of the ray beam from the border region of the ray beam situated opposite to the rotation direction towards the border region of the ray beam situated in the rotation direction. This procedure is preferably used in a 180° scan for the single ray beam, for example.

For example, if two ray beams are used in a 90° scan, the fan angles of these two ray beams can likewise be increased or, respectively, decreased in the manner described in the preceding. However, in this case a somewhat modified increase or decrease mode can advantageously be provided.

For the first ray beam the increase of the value of the fan angle again ensues by a blending in of rays of the ray beam from a border region of the ray beam that is situated opposite to the rotation direction toward a border region of the ray beam situated in the rotation direction. However, the decrease of the value of the fan angle ensues by a masking of rays of the first ray beam from the two border regions towards a central region of the first ray beam—i.e. from the two border regions to the central region. The increase thereby ensues continuously or quasi-continuously, step-by-step, in contrast to which the decrease ensues in an abrupt manner, thus in a single step.

For the second ray beam the decrease of the value of the fan angle ensues by a blending in of rays of the ray beam from a central region of the second ray beam toward border regions of the second ray beam that are situated in the rotation direction and opposite to the rotation direction. The decrease of the value of the fan angle ensues by a masking of rays of the ray beam from the border region of the ray beam that is situated opposite the rotation direction toward the border region of the ray beam that is situated in the rotation direction. The decrease preferably ensues continuously or quasi-continuously, step-by-step, in contrast to which the decrease ensues in an abrupt manner, thus in a single step.

In all cases the increase and the decrease of the fan angle of the different radiation sources are coordinated by a suitable controller.

DESCRIPTION OF THE PREFERRED EMBODIMENTS

Figure 1:
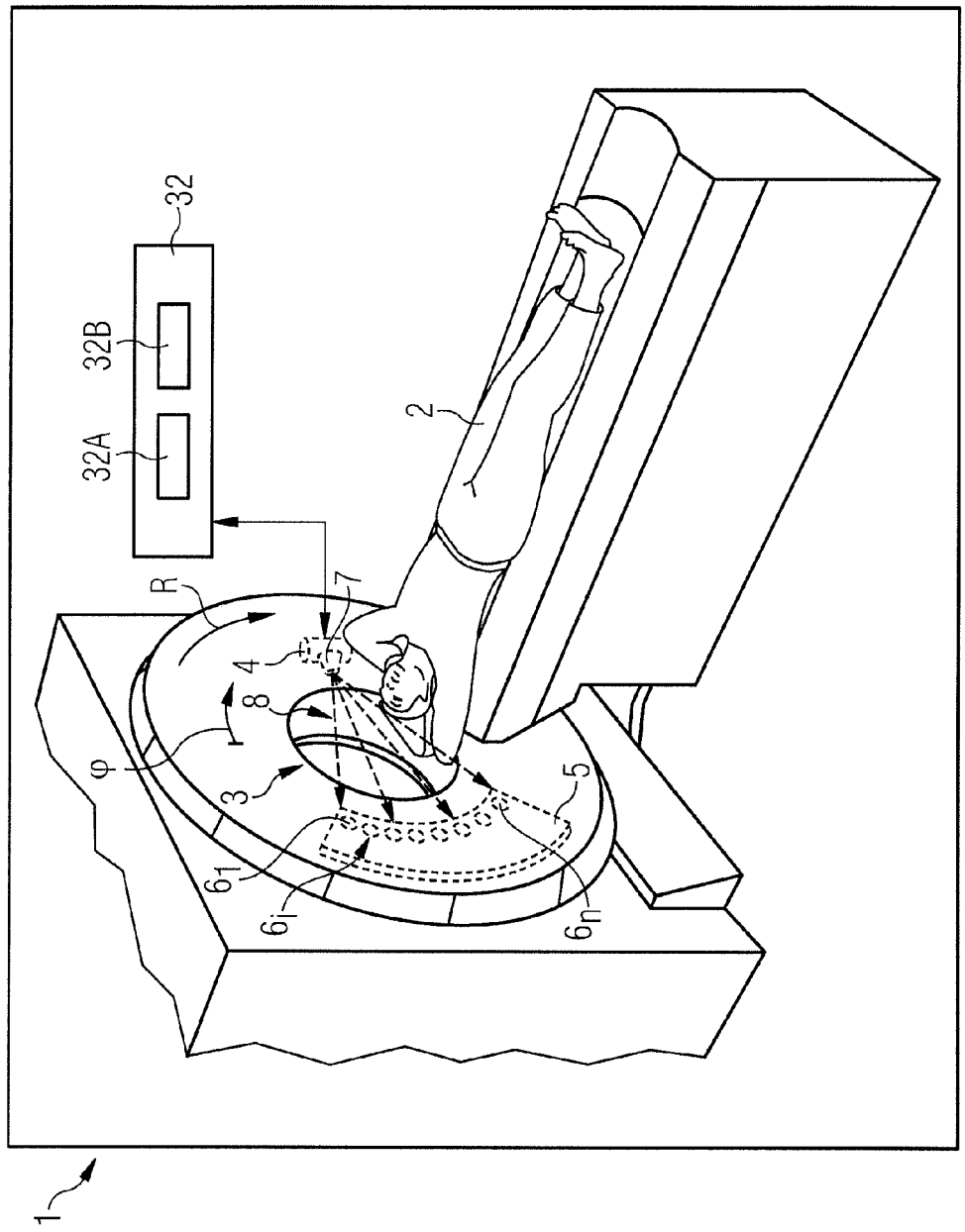
FIG. 1 schematically illustrates a CT device according to the prior art and a ray beam with a constant fan angle that is generated with said CT device.
Figure 2:
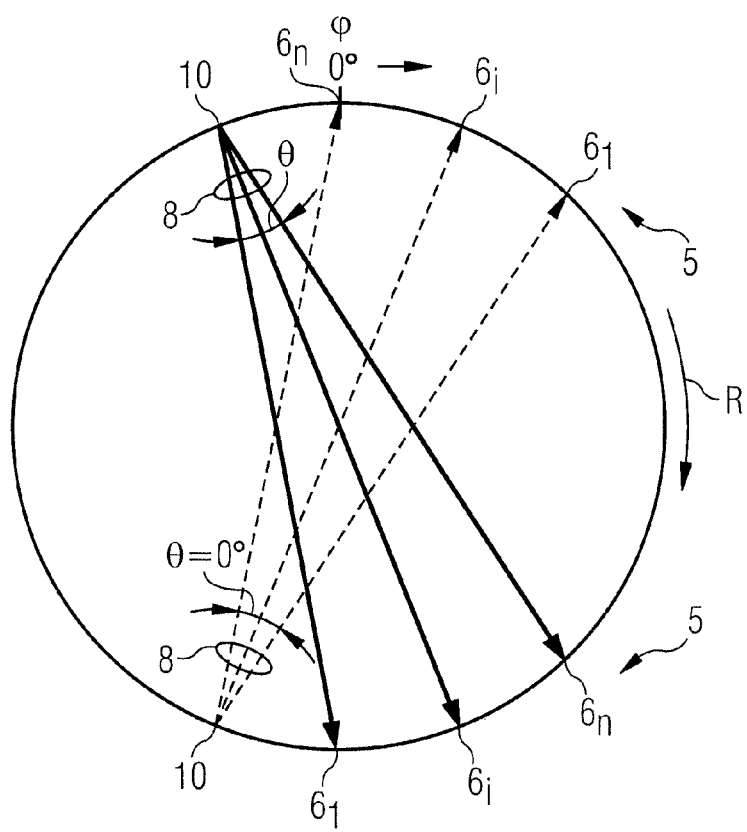
FIG. 2 shows the ray beam according to FIG. 1 at two rotation angle positions.
Figure 23:
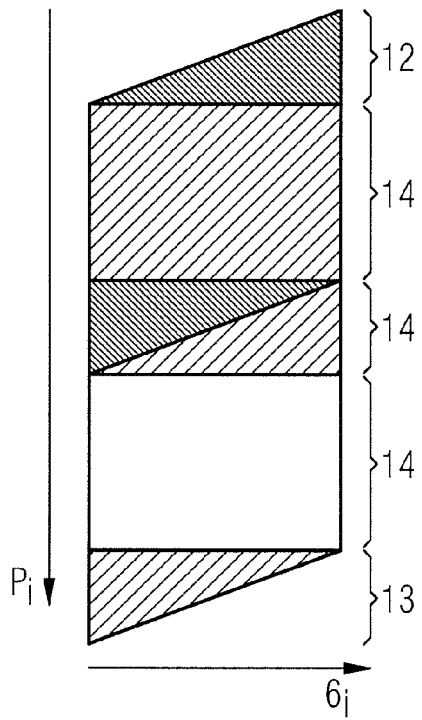
FIG. 23 is a sinogram for a dual-source CT device according to the prior art.

In contrast to the diaphragm device 7 described above in connection with the CT device 1 according to FIG. 1, the CT device 1 according to the invention that is shown in FIG. 23 has a diaphragm device 7 that is fashioned to vary the fan angle θ. This is achieved by a diaphragm device 7 that is to be opened and closed asymmetrically relative to the center of the ray beam 8, which is discussed in detail in the following. Furthermore, the control device 32 is equipped with a diaphragm control module 32C that is fashioned to control the value of the fan angle θ (thus ultimately the diaphragm device 7 or its configuration) depending on the rotation angle φ.

Figure 4:
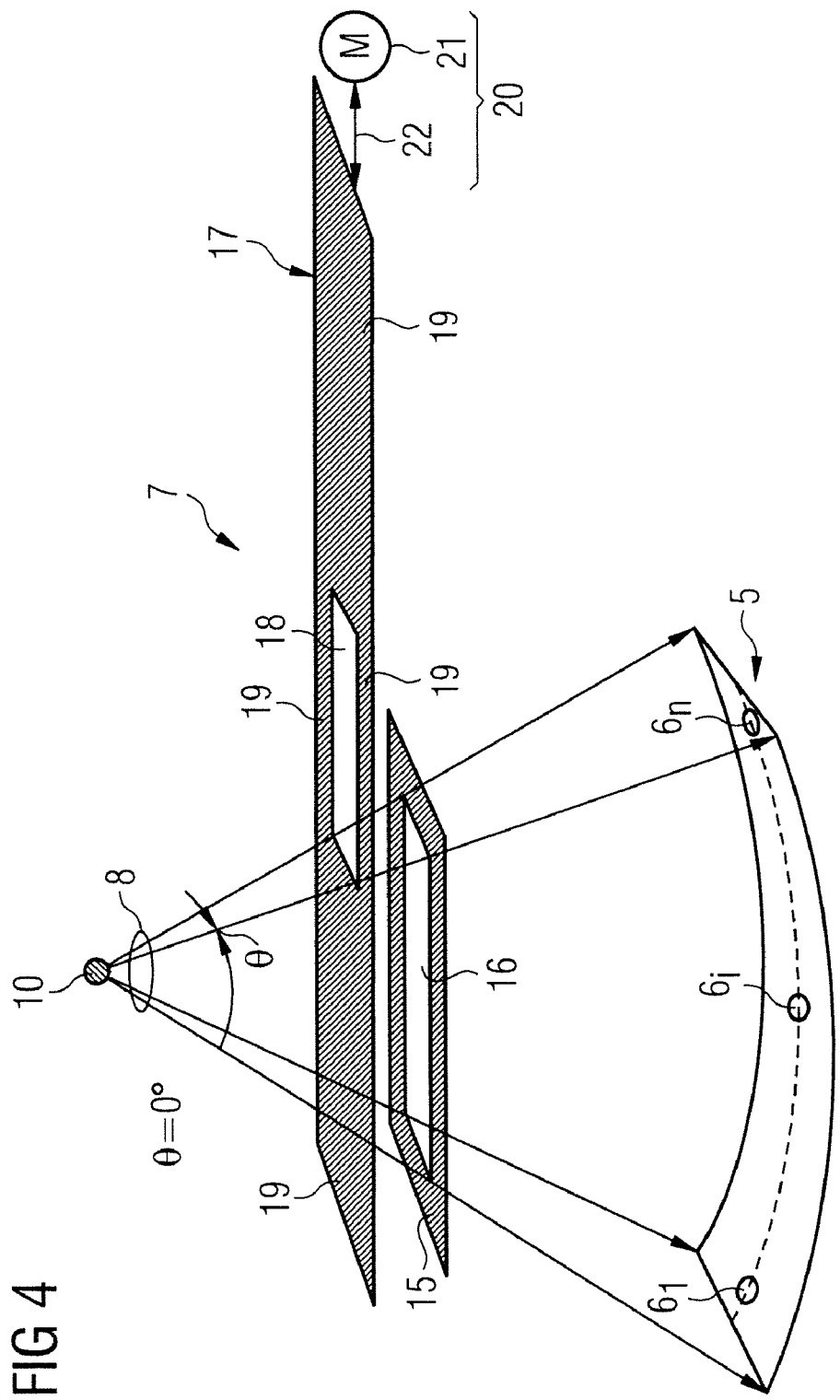
FIGS. 4 through 6 respectively show different configurations of a diaphragm device for a CT device according to the invention, according to a first exemplary embodiment of the invention.
Figure 5:
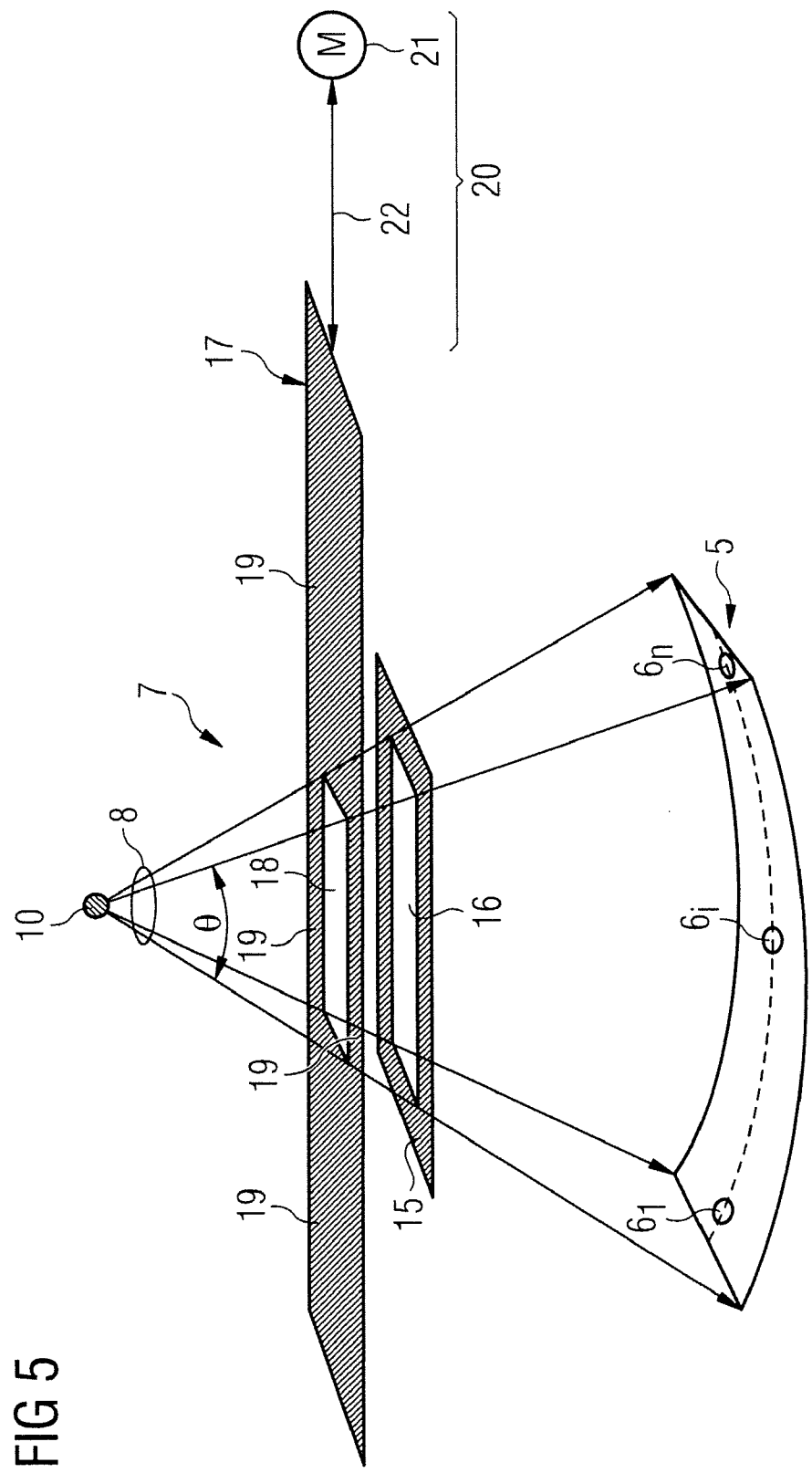
Figure 6:
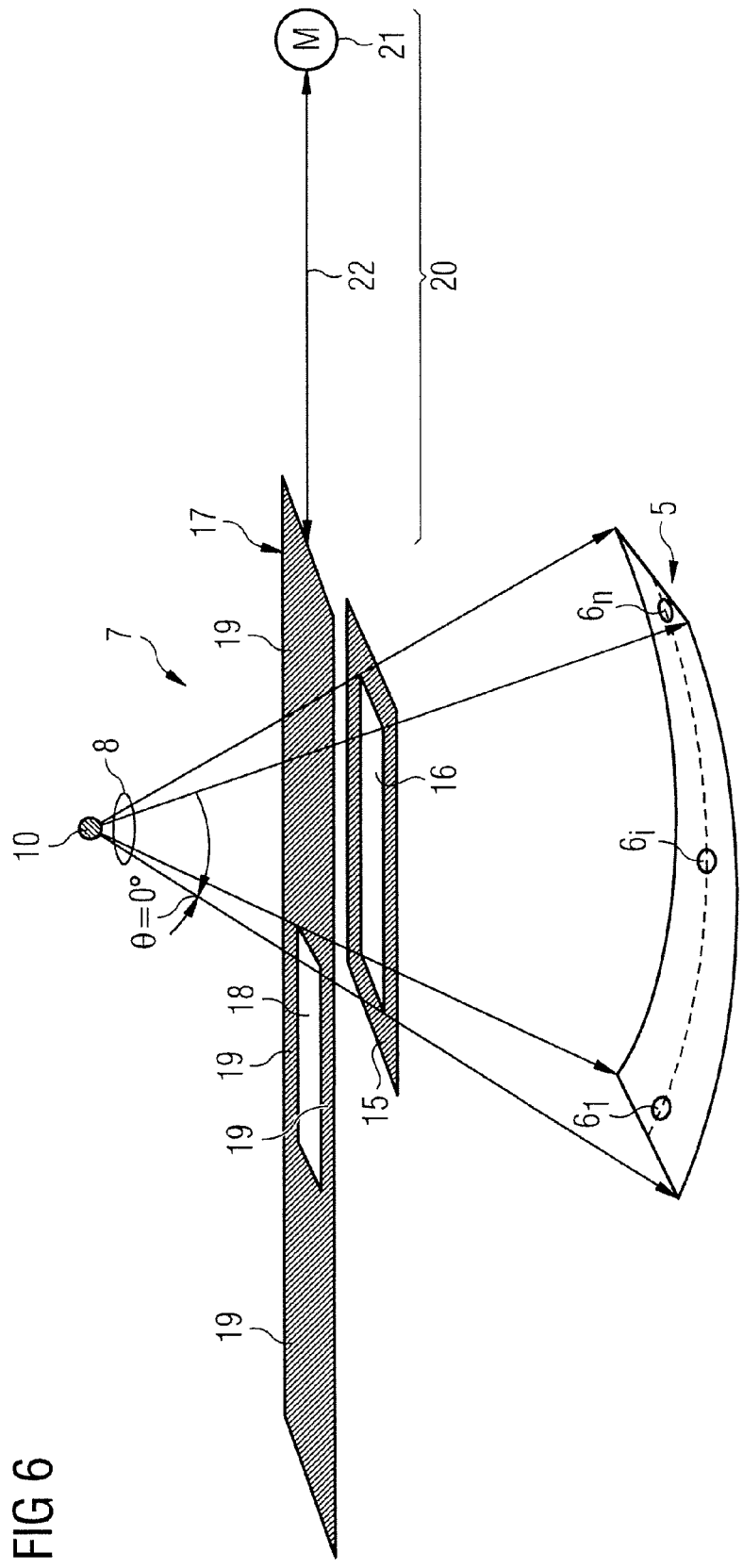

A realization of the diaphragm device 7 is roughly schematically reproduced in FIGS. 4 through 6. The diaphragm device 7 has a first slit diaphragm 15 that is fixed in relation to the focus 10, which slice diaphragm 15 has a diaphragm aperture (in the present case a first diaphragm slit 16) that is dimensioned such that a maximum value of the fan angle θ of the ray beam 8 is defined with the aid of the first diaphragm slit 16. In the present case, the maximum value is dimensioned such that the detection-capable range of the detector system 5 (thus all channels $6_i$) can be exposed. The diaphragm device 7 furthermore has at least one additional diaphragm part that is dimensioned such that the value of the fan angle θ can be affected between a start value and an end value.

In the exemplary embodiment, the start value is 0° and the end value is 50°, wherein other values can be used depending on the application case and geometry, however. The second diaphragm part possesses a second slit diaphragm 17 that is movable relative to the first slit diaphragm 15. The second slit diaphragm 17 has a radiation-permeable second diaphragm slit 18 and radiation-impermeable delimitation regions 19 on both sides of the second diaphragm slit 18. For the sake of completeness it is noted that these delimitation regions 19 also delimit the second diaphragm slit 18 in the longitudinal direction.

The delimitation regions 19 located in the movement direction of the second slit diaphragm 17 are dimensioned so that they can completely cover the first diaphragm slit 16 and therefore the ray beam 8 is completely shielded, as this is depicted in FIGS. 4 and 6. As is apparent from FIG. 5, the dimensions of the second diaphragm slit 18 are selected so that the ray beam 8 can unfold completely given a positional coincidence of the first diaphragm slit 15 and the second diaphragm slit 18.

The second slit diaphragm 17 is mounted such that it can shift past the first slit diaphragm 15. In the present case this ensues in a plane parallel or slightly curved relative to the flat or slightly curved extent of the first slit diaphragm 15. In order to implement the movement, the first slit diaphragm is coupled with a first actuation stage 20. The first actuation state 20 has a first motor 21 whose output drive is converted into translational first movements 22 of the second slit diaphragm 18.

Figure 7:
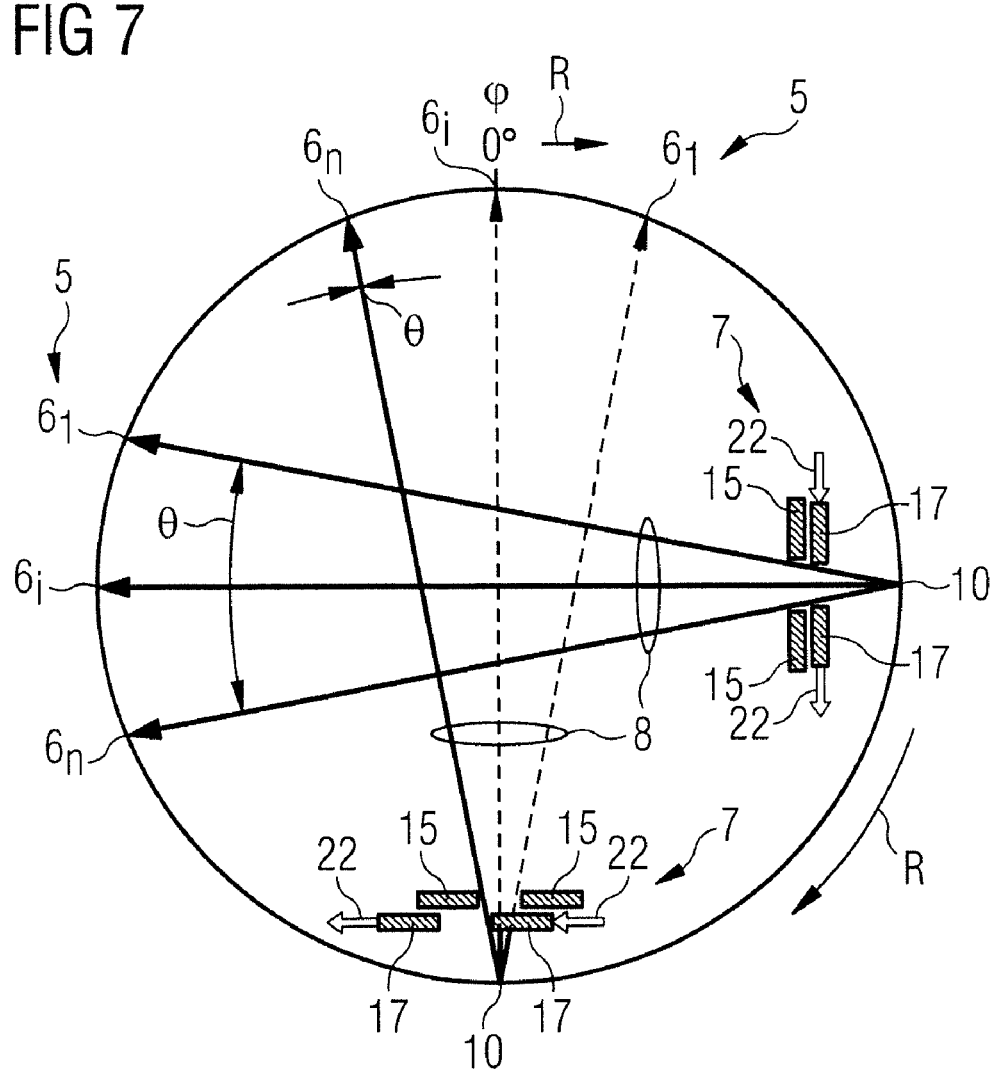
FIG. 7 shows a ray beam generated at two rotation angle positions with the use of the diaphragm device according to FIG. 4.

The relative positions of the two slit diaphragms 15 and 17 are schematically shown in FIG. 7 as representative of two values of the rotation angle φ (namely 90° and 180°). For the ray beam 8, three rays are respectively shown, namely at the border region in a rotation direction R, at the border region opposite the rotation direction R and in the center of the ray beam. A solid line thereby indicates a non-masked ray and an interrupted line indicates a masked ray.

The function of the diaphragm device 7 according to the invention is described in the following using the sequence of FIGS. 8 through 16 in the form of a radioscopy method according to the invention. In FIGS. 8 through 15 the numbered arrow respectively symbolizes the continuation of the sequence in the next figure.

Figure 8:
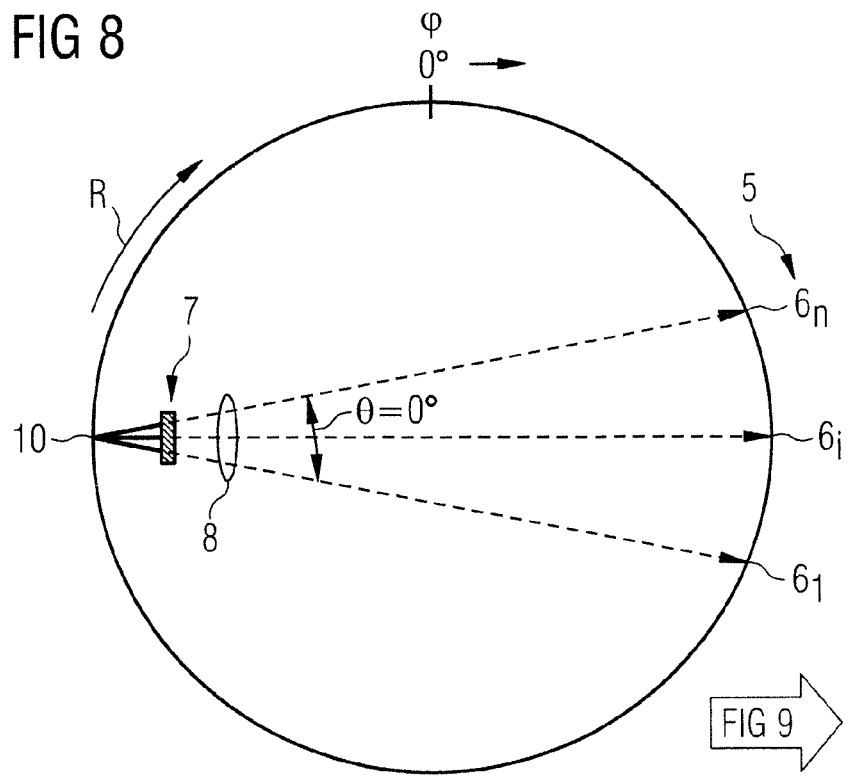
FIGS. 8 through 16 show the response of a fan angle of the ray beam during a rotation of the diaphragm device for a single-source CT device, depending on the rotation angle position of the diaphragm device according to FIG. 4.

In FIG. 8 the diaphragm device 7 is initially shown at a position that corresponds to a rotation angle φ with a value of −90°. The ray beam 8 is masked completely via a complete covering of the first diaphragm slit 15 by the delimitation region 19 of the second slit diaphragm 17. This corresponds to the configuration of the two slit diaphragms 15 and 17 that is shown in FIG. 4.

Figure 9:
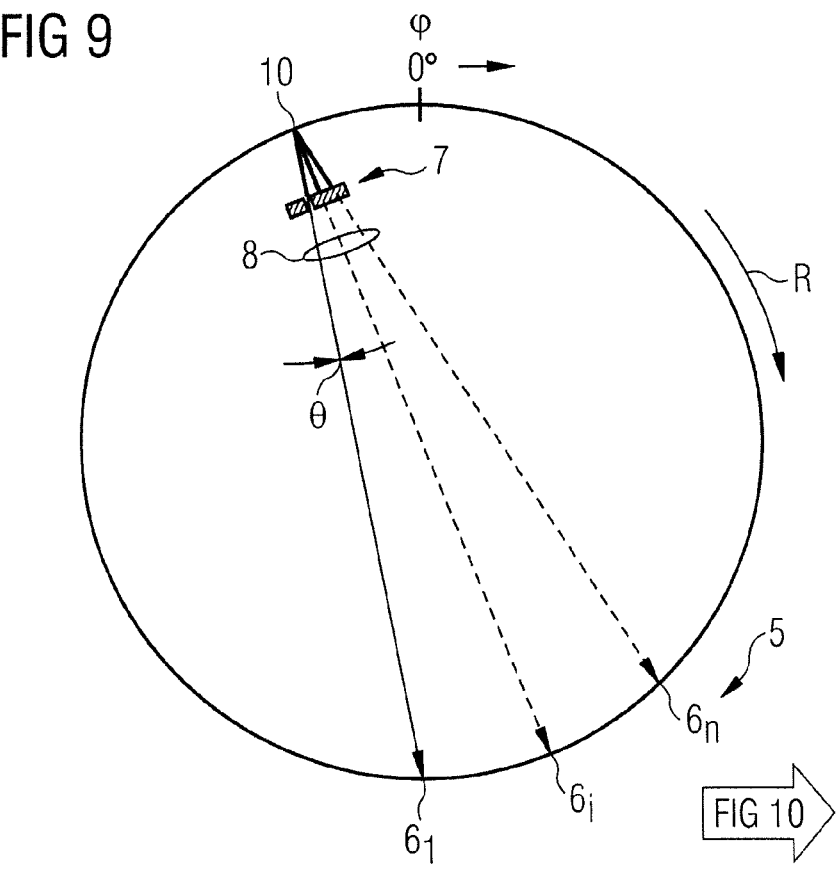
Figure 10:
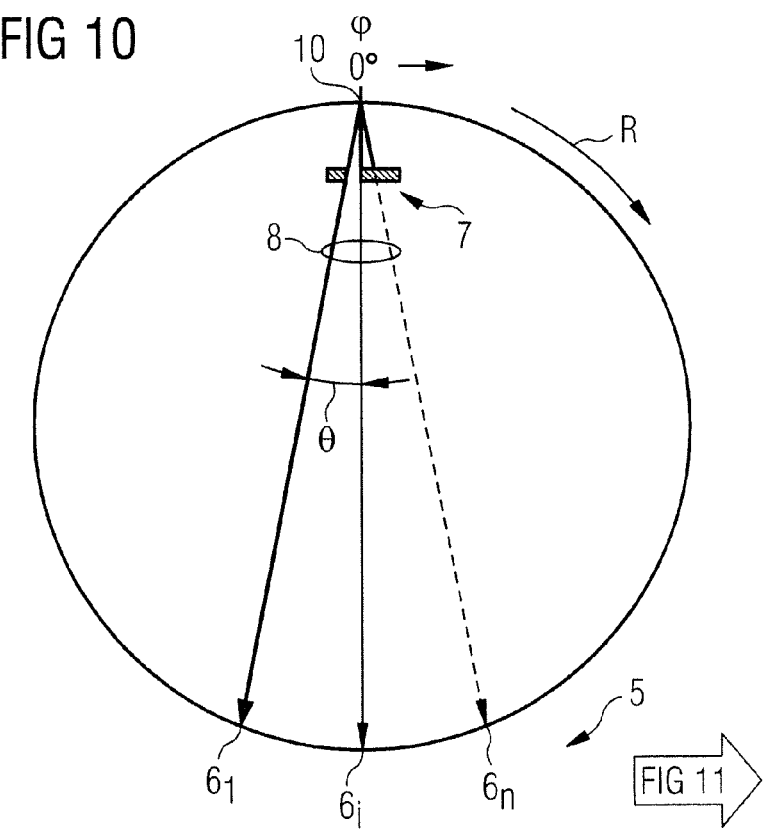
Figure 11:
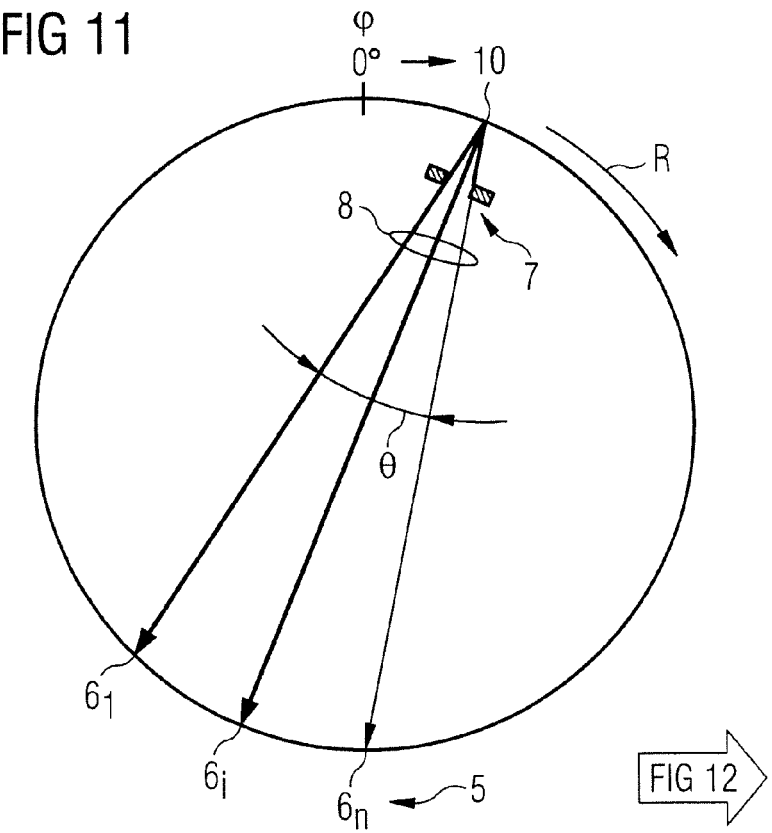
Figure 12:
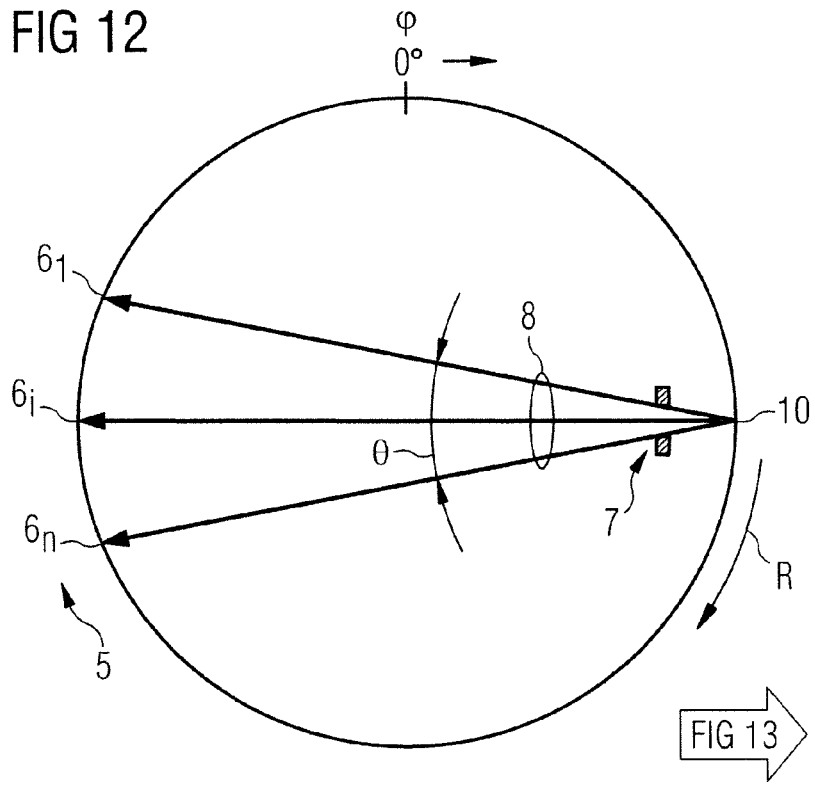

As soon as the diaphragm device 7 assumes a rotation angle φ with a value of −(θ/2)—see FIG. 9—the second slit diaphragm is moved so far that the value of the fan angle θ is set such that the focus 10 exhibiting a final expansion is projected onto the first channel $6_1$. In the course of the further movement of the diaphragm device 7, the value of the fan angle θ is increased further until finally at φ=0° (see FIG. 10) half of the maximum value of the fan angle θ is reached, such that approximately half of the channels $6_i$ are exposed. Finally (see FIG. 11) the maximum value of the fan angle θ is reached given a value of the rotation angle of φ=+θ/2. The two slit diaphragms 15 and 17 thereby occupy positions relative to one another as shown in FIG. 5. As of this value of the rotation angle φ all channels $6_i$ are exposed, which is shown in a representative manner for additional values of the rotation angle φ given a value of +90° in FIG. 12.

Figure 13:
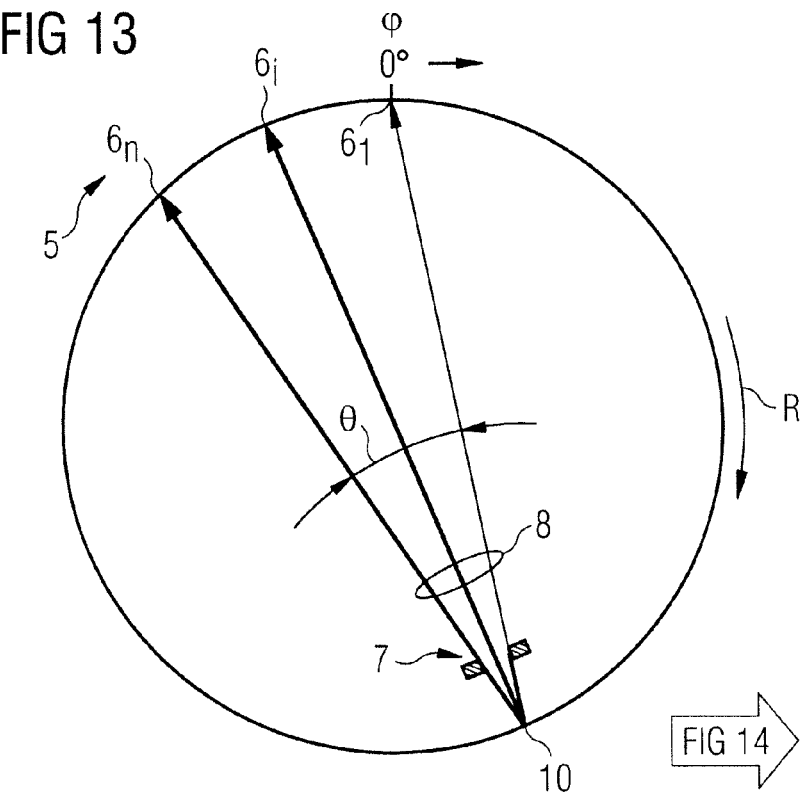
Figure 14:
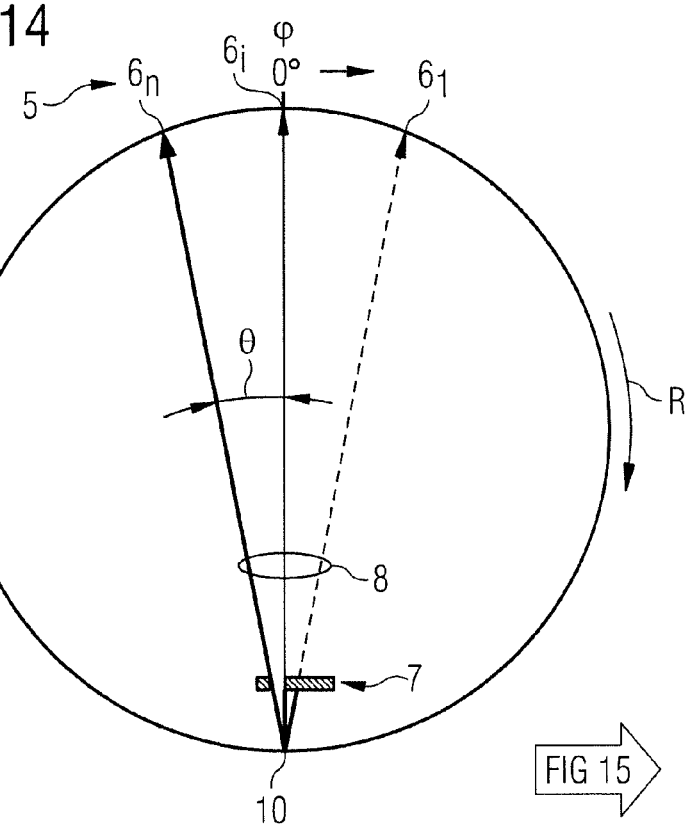
Figure 15:
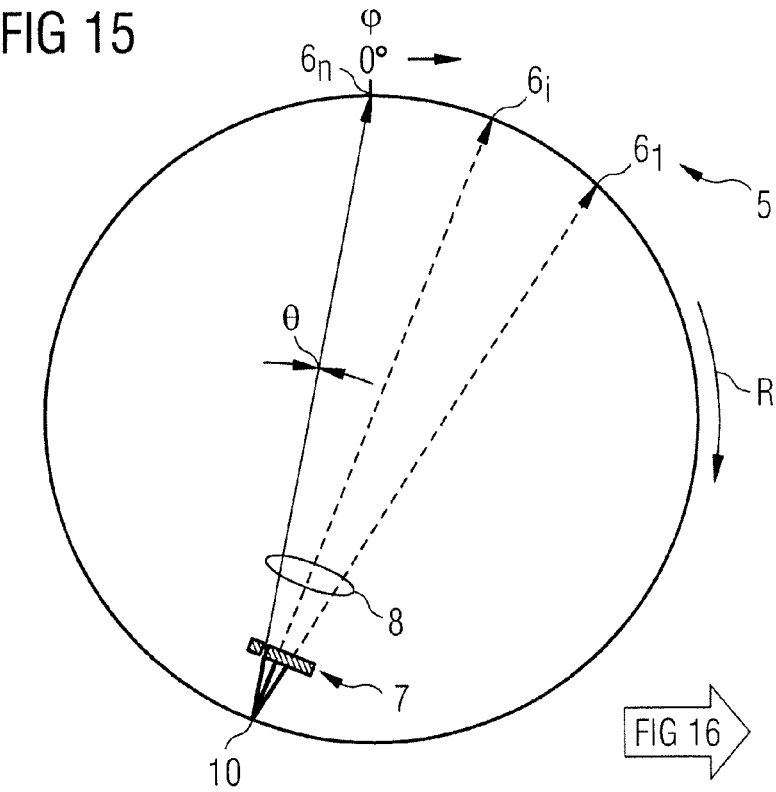

This aforementioned relative position of the two slit diaphragms 15 and 17 is maintained until the diaphragm device 7 has reached a rotation angle φ with a value of φ=90°−θ/2 (see FIG. 13). If this value is exceeded, the exposure of the channels $6_i$ is adjusted in order, beginning with the first channel $6_1$. This is achieved by a decrease of the fan angle θ. For this, given a continuous rotation of the diaphragm device 7 the delimitation region 19 of the second slit diaphragm 17 is shifted continuously in front of the first diaphragm slit 16 until finally, upon reaching a rotation angle φ with a value of 180°, the fan angle θ exhibits only half of the maximum value any more (see FIG. 14). Ultimately, the value of the fan angle θ is adjusted given a value of the rotation angle φ of 180°+θ/2 such that the focus 10 is only projected on the last channel $6_n$ any more (see FIG. 15).

Figure 16:
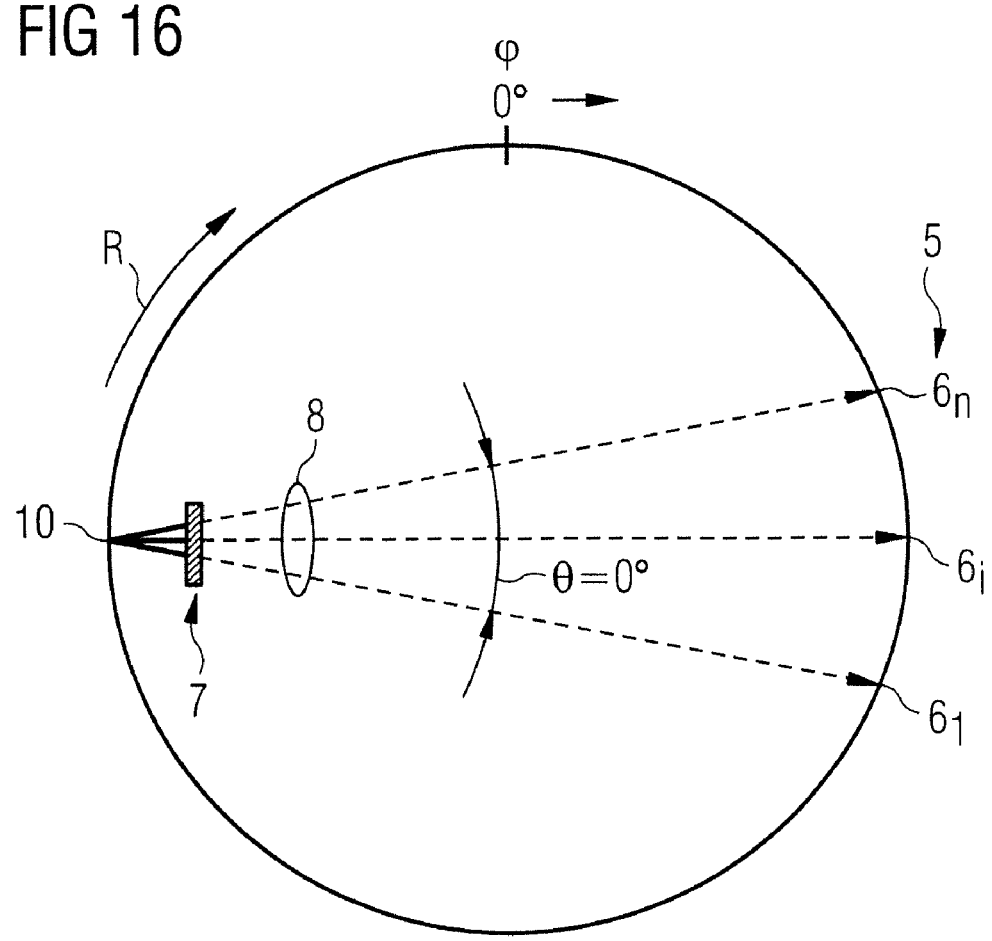

Upon exceeding the value of the rotation angle φ of 180°+θ/2, the delimitation region 19 of the second slit diaphragm 17 completely covers the first diaphragm slit 16 (as this is shown in FIG. 6) and the ray beam 8 is completely masked (see FIG. 16).

According to a further exemplary embodiment of the invention, the at least one further diaphragm part has a movable first plate or bar 23 and a movable second plate or bar 24 of a plate (bar) diaphragm 25. The two plates 23 and 24 respectively form a radiation-impermeable region. Even if preferably completely radiation-impermeable regions are desired, at this point it is noted that under certain circumstances incompletely radiation-impermeable regions can also exist.

In order to enable a movement of the two diaphragms plates 23 and 24, each of them is coupled with a separate actuation stage, namely a second actuation stage 26 and a third actuation stage 27. The second actuation stage 26 has a second motor 28 whose output drive is converted into translational second movements 30 of the first plate 22. The third actuation stage 27 has a third motor 29 whose force effect is converted into translational third movements 31 of the second plate 24. The motors can be controlled independent of one another and accordingly also enable a movement of the two plates 23 and 24 independent of one another. In the present case the motors are executed as step motors and are coordinated or operated synchronized with one another. However, they can also be realized as other types of motors.

Figure 17:
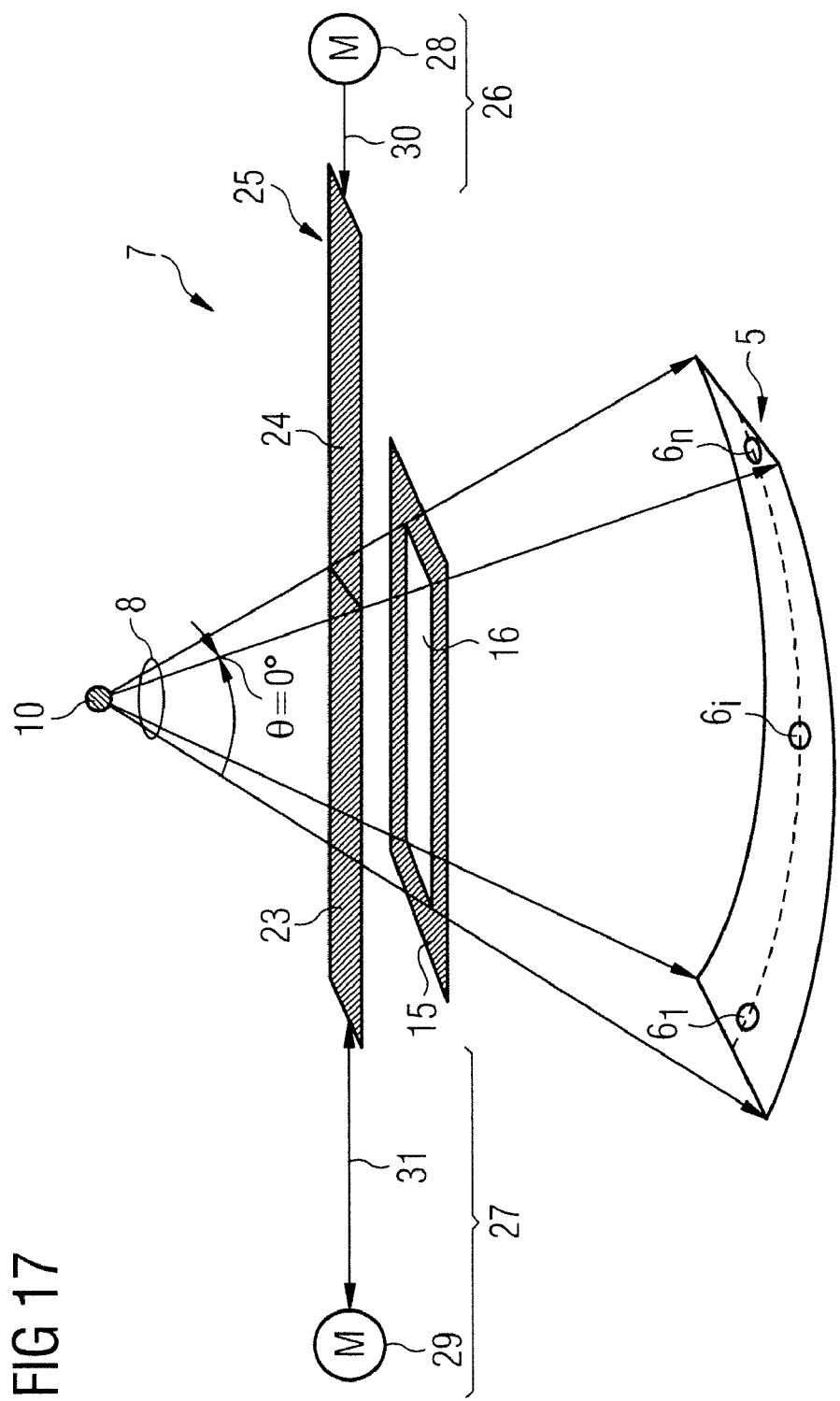
FIGS. 17 through 21 respectively show different configurations of a diaphragm device for a CT device according to the invention according to a second exemplary embodiment of the invention.
Figure 18:
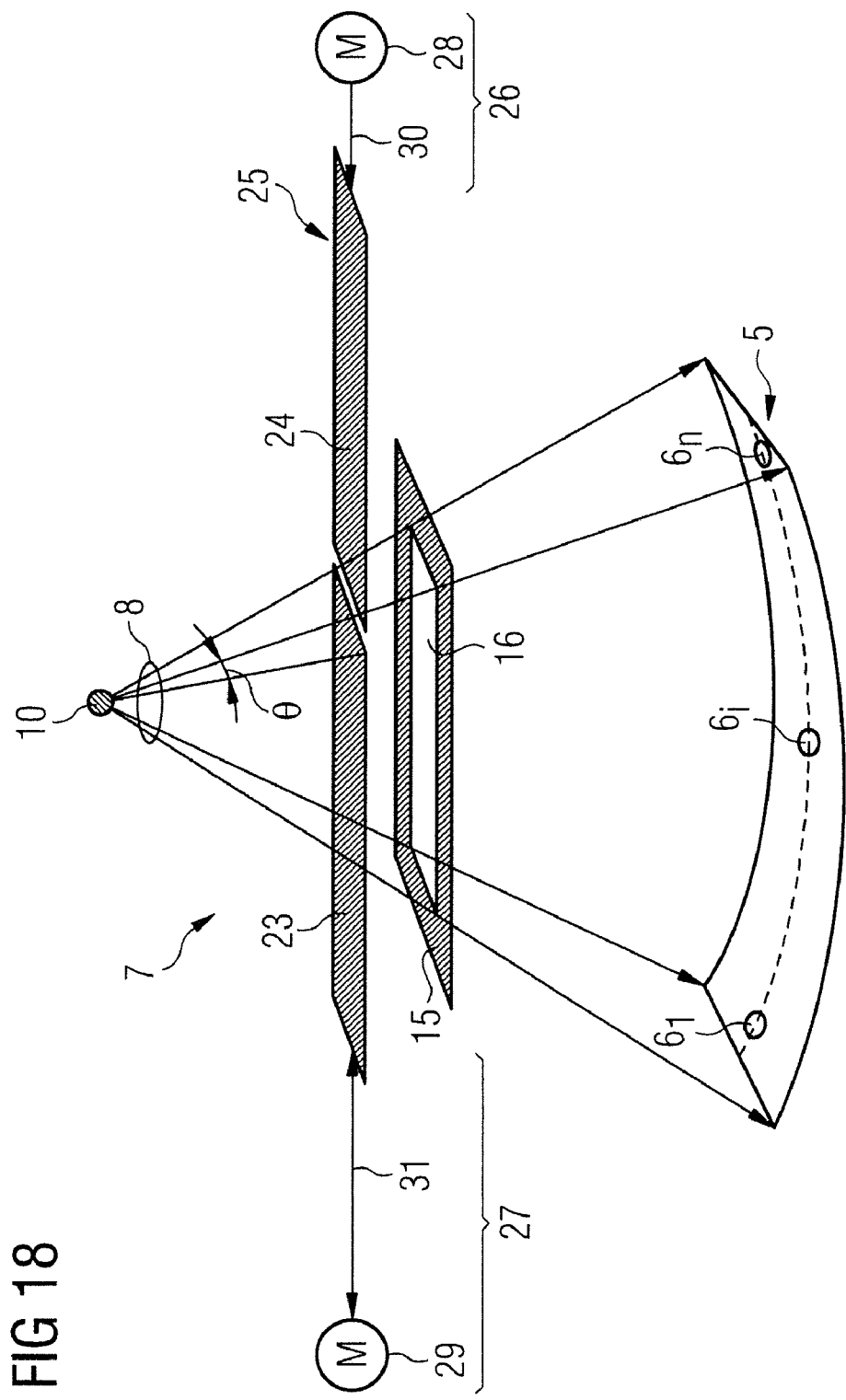
Figure 19:
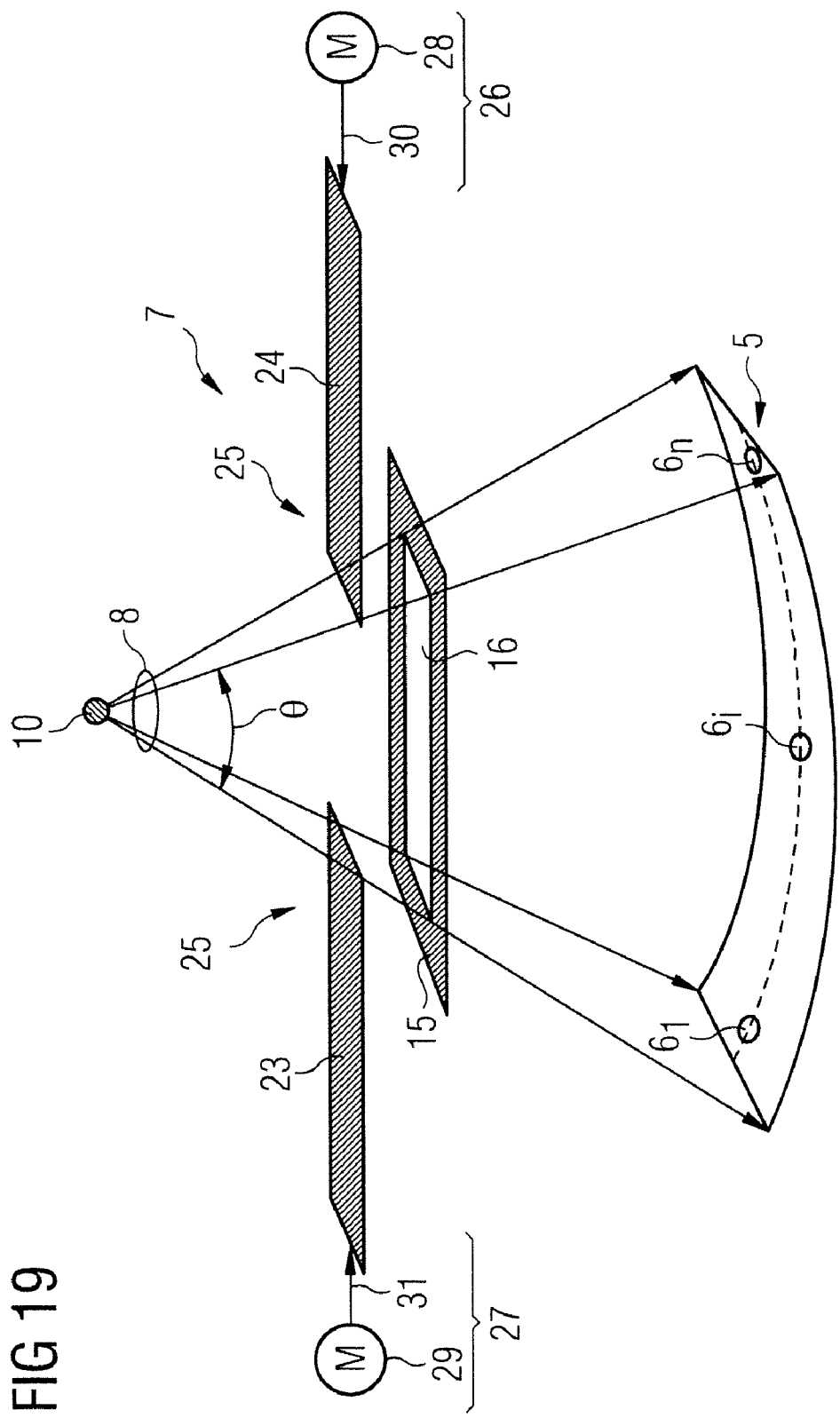
Figure 20:
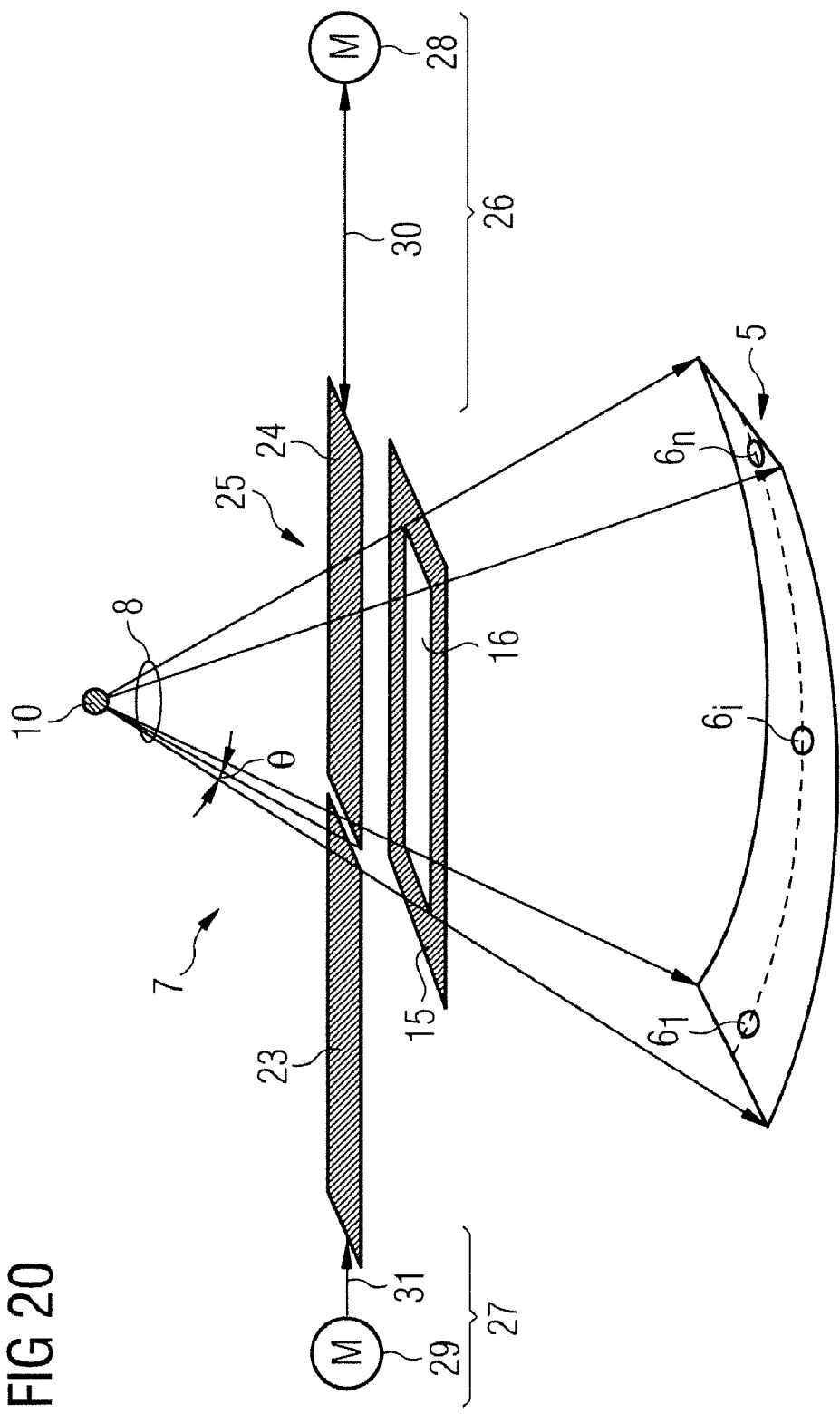
Figure 21:
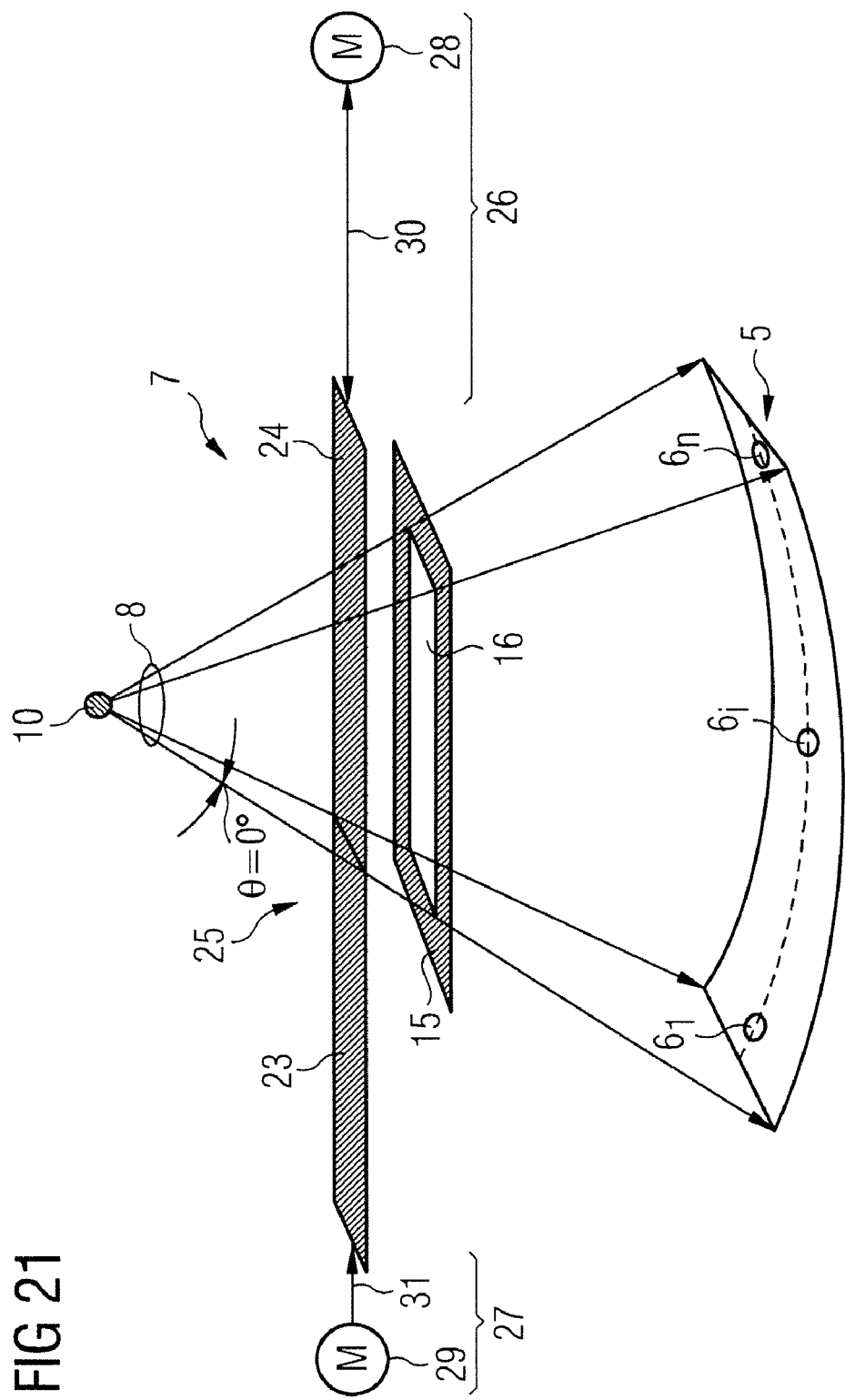
Figure 22:
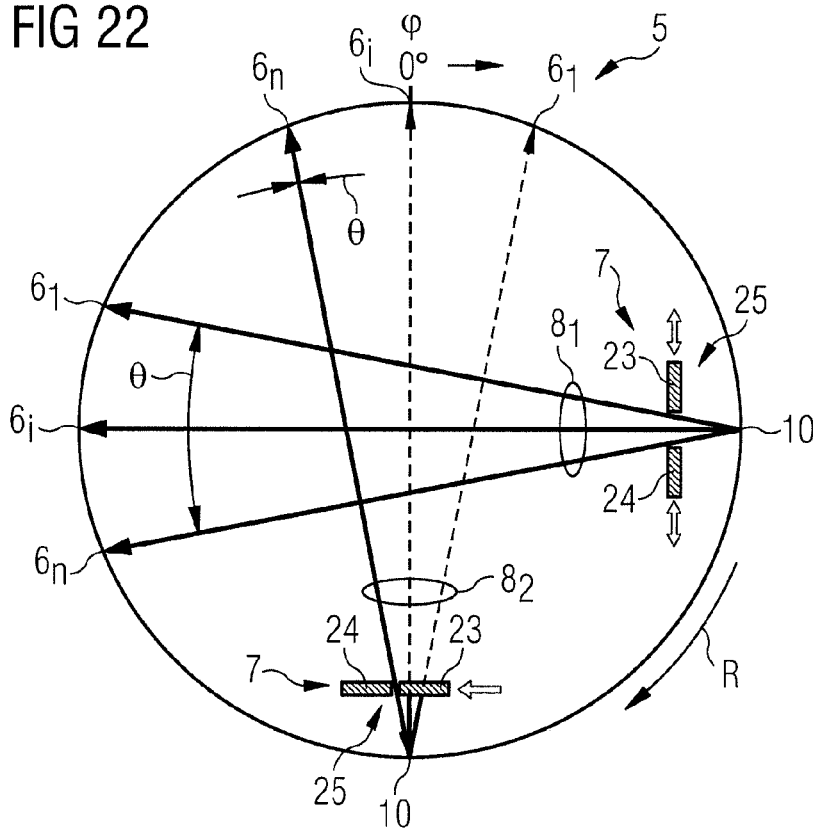
FIG. 22 shows a ray beam generated at two rotation angle positions with the aid of the diaphragm device according to FIG. 17.

The dimensions of the two plates 23 and 24 are selected so that they completely cover the first diaphragm slit 16 when they are located in extreme positions according to FIG. 17 and FIG. 21. The two actuation stages 26 and 27 cause the two plates 23 and 24 to be moved between these two extreme positions in a plane parallel to the first slit diaphragm 15, as this is shown in FIGS. 18 through 20 for three different positions. Analogous to FIG. 7, the positions of the two plates 23 and 24 relative to one another is schematically shown in a representative manner in FIG. 22 for the two values of the rotation angle $\phi$ of 90° and 180°. With this realization of the diaphragm device 7, the fan angle $\theta$ can also be affected during the rotation of the diaphragm device 7, as this was illustrated with the aid of FIGS. 8 through 16.

It is now discussed again in detail that, at the start of the blending (mixing) in of the ray beam (at the start of the scan), only the first channel $6_i$ situated at a first position in the rotation direction is exposed, and in the further course of the rotation additional channels $6_i$ through $6_n$ situated further on in the rotation direction are successively added by increasing the value of the fan angle $\theta$ of the ray beam or—expressed in another way—are exposed by the widening ray beam $\theta$ in addition to preceding channels $6_i$.

In contrast to the increase, the decrease of the value of the fan angle $\theta$ is begun with the masking of the first channel $6_1$ and, in the further course of the rotation, channels $6_i$ to a last channel $6_n$ that lie further along in the rotation direction are successively omitted by reducing the value of the fan angle $\theta$ of the ray beam 8 or—expressed in another way—are no longer exposed by the narrowing ray beam 8.

The point in time of the blending or masking of each additional channel $6_i$ ultimately depends on the rotation speed, such that the additional channels $6_i$ are blended in or masked out in a quicker sequence given a higher rotation speed and are blended in or masked out in a slower sequence given a lower rotation speed.

According to a further exemplary embodiment—analogous to the CT device 1 equipped with a single x-ray source 4—each of the two ray beams 8 is blended in (added to), overlapping, at the beginning of the scan, or the value of the fan angle $\theta$ is increased, and at the end of the scan the two ray beams 8 are masked out so the value of the fan angle $\theta$ is decreased.

Figure 32:
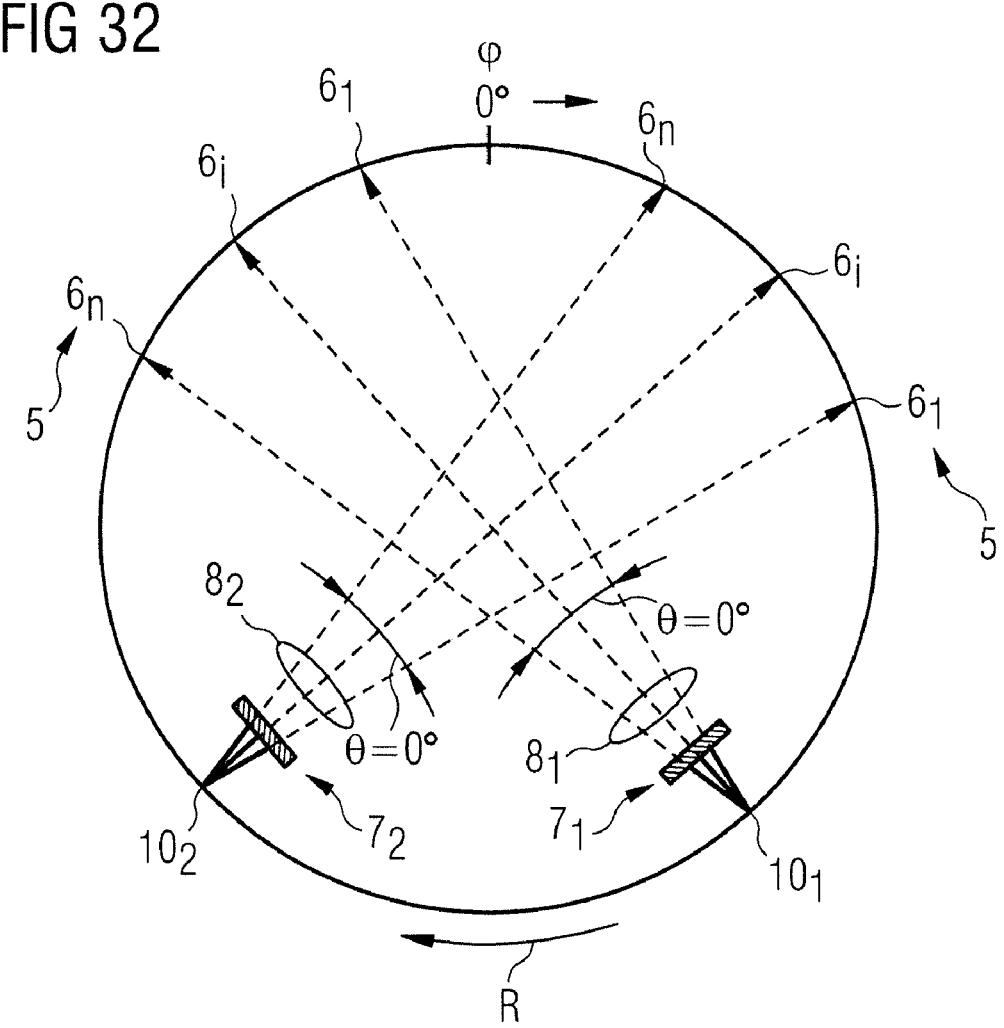

An additional exemplary embodiment is discussed in detail using FIGS. 24 through 32, wherein the numbered arrow in FIGS. 24 through 31 again respectively symbolizes the continuation of the sequence in the next Figure. Even if the two ray beams 8 and the two diaphragm devices 7 are realized identically or are identically parameterized in the following, for reasons of expediency in the following separate reference is made to a first ray beam $8_1$ and a second ray beam $8_2$, a first diaphragm device $7_1$ and a second diaphragm device $7_2$ and a first focus $10_1$ and a second focus $10_2$.

Figure 24:
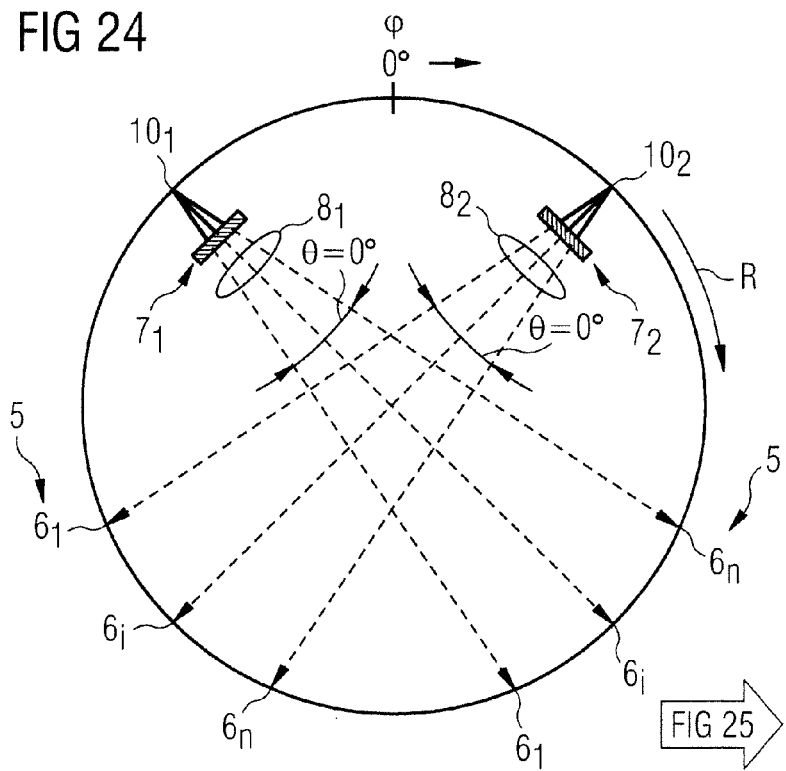
FIGS. 24 through 32 show the response of a fan angle of the ray beam during a rotation of the diaphragm device for a dual-source CT device, depending on the rotation angle position of the diaphragm device according to FIG. 4.
Figure 25:
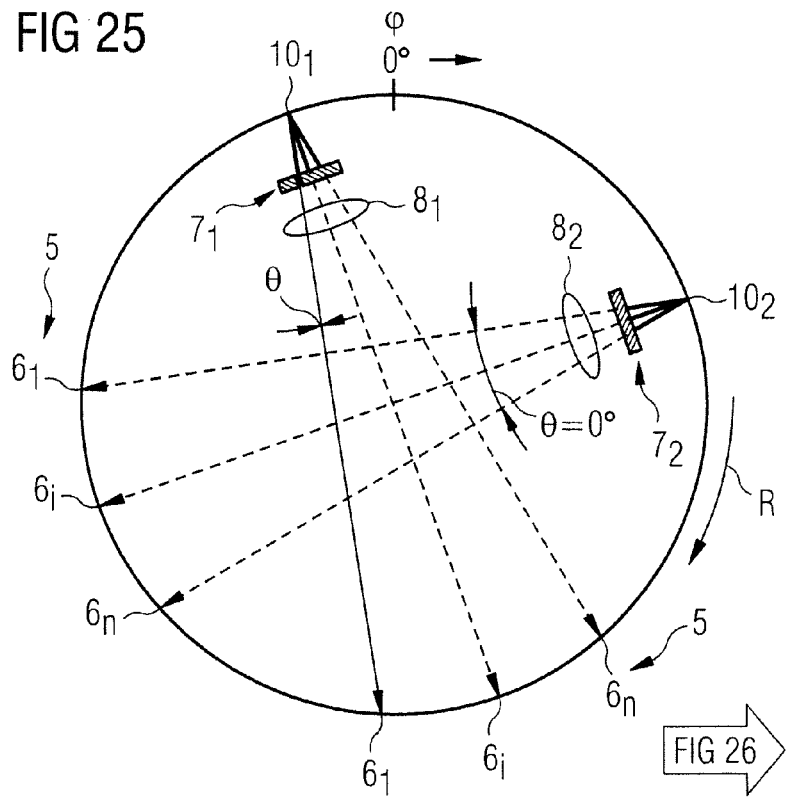
Figure 26:
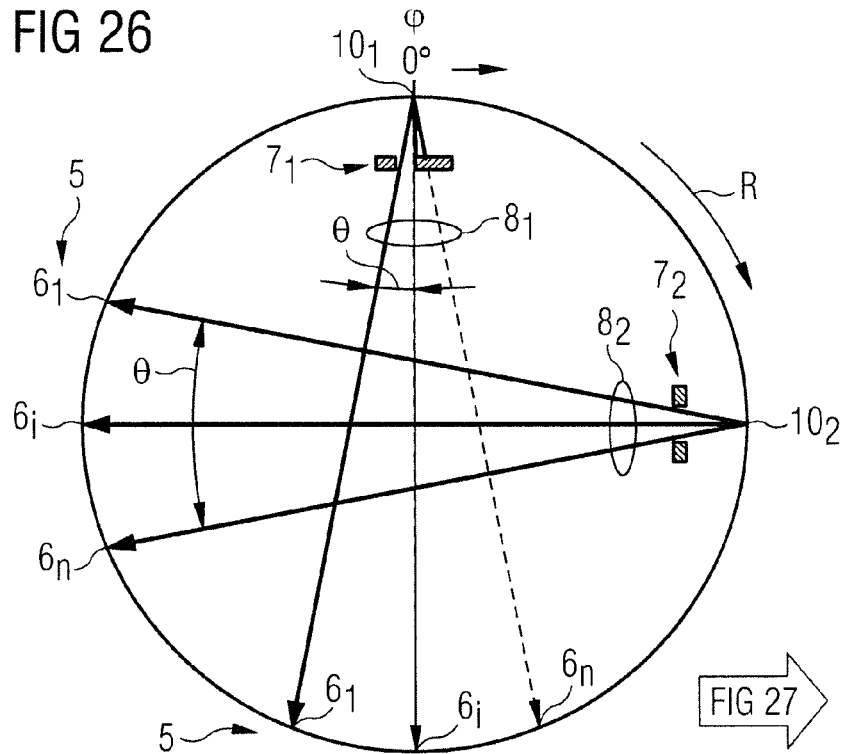

Assuming a situation shown in FIG. 24, in which both ray beams $8_1$ and $8_2$ are masked out or, respectively, are shielded by the diaphragm devices $7_1$ and $7_2$, the two diaphragm devices $7_1$ and $7_2$ are rotated counter-clockwise synchronously with one another since they are attached to the gantry 9 before the respective x-ray source 4. The opening of the first diaphragm device $7_1$—thus consequently the increase of the value of the fan angle $\theta$ (see FIG. 25)—begins as soon as the first focus $10_1$ reaches a position at which the value of the rotation angle $\phi$ corresponds to half of the negative value of the fan angle $\theta$. In the further course of the rotation the second diaphragm device $7_2$ remains closed until the rotation angle $\phi$ relative to the first focus $10_1$ has a value of 0° (see FIG. 26). At this point in time the second focus $10_2$ is located at a position that corresponds to a value of the rotation angle of 90°. Upon reaching this position the second diaphragm device $7_2$ abruptly increases the second ray beam $8_2$ with the maximum value of the fan angle $\theta$ from the center of the second ray beam $8_2$ up to the border regions.

Figure 27:
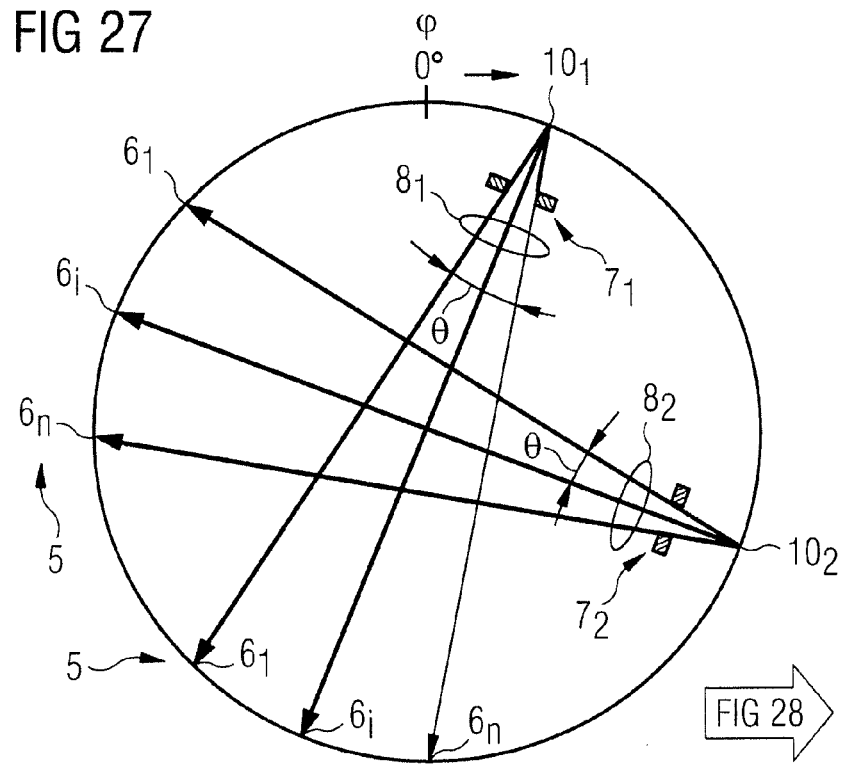
Figure 28:
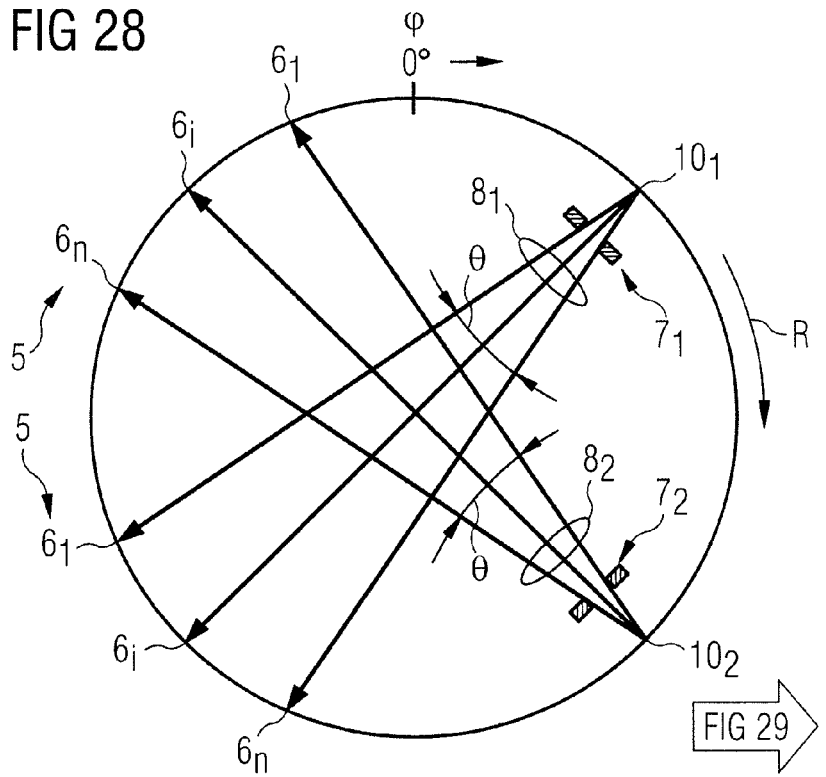

In the course of the further rotation, the second diaphragm device $7_2$ remains completely open while the increase of the value of the fan angle $\theta$ for the first ray beam $8_1$ increases until the rotation angle $\phi$ relative to the first focus $10_1$ has a value of $+\theta/2$ (see FIG. 27). As of this value of the rotation angle, both diaphragm devices $7_1$ and $7_2$ are completely open, which is shown in FIG. 28 for a value of the rotation angle $\phi$ of 45° relative to the first focus $10_1$.

Figure 29:
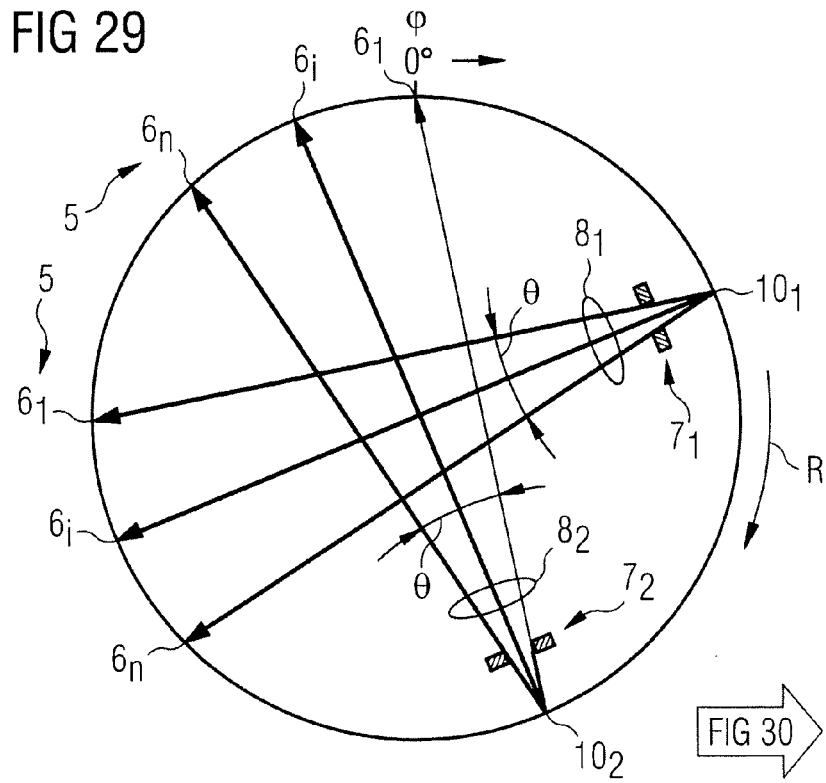
Figure 30:
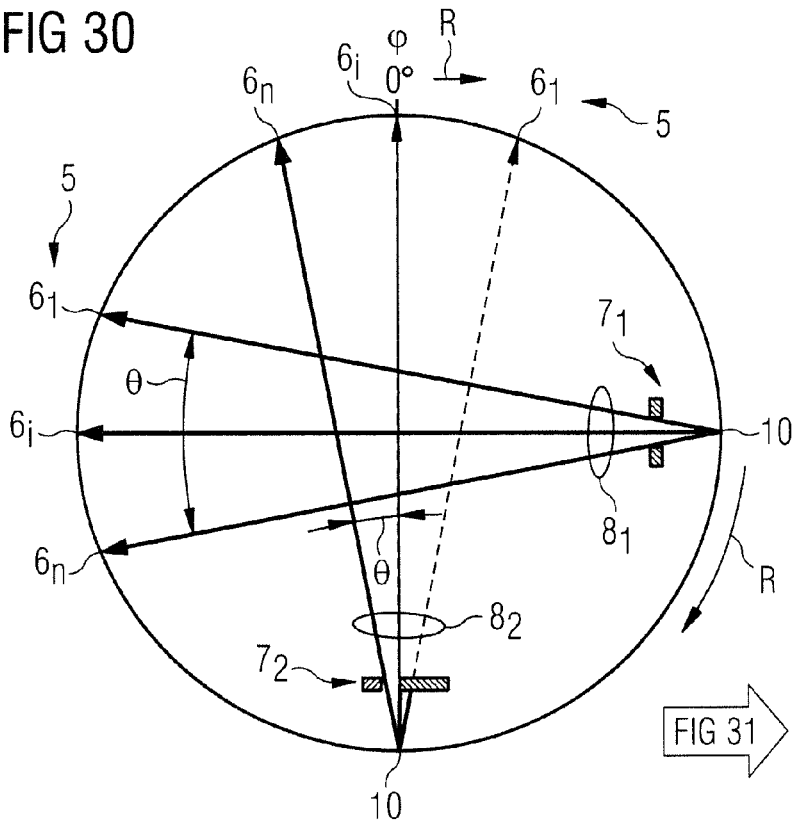
Figure 31:
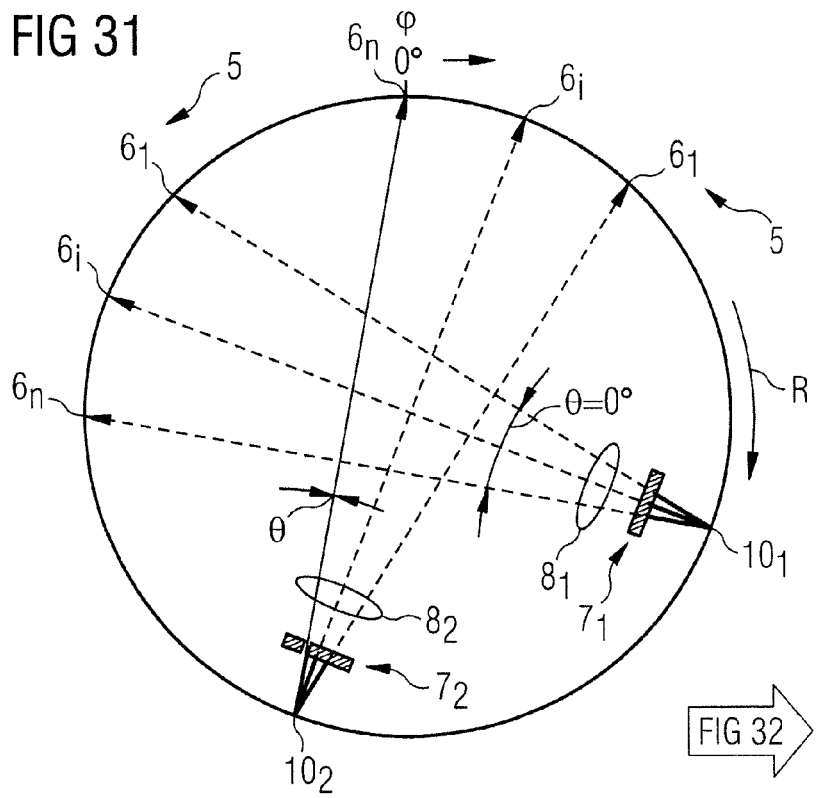

However, as soon as this rotation angle $\phi$ exceeds the value of $\phi=90°-\theta/2$ the decrease of the value of the fan angle $\theta$ begins for the second ray beam $8_2$ (see FIG. 29). In the course of the rotation by an additional value of $\theta/2$, the fan angle $\theta$ is reduced to half of its maximum value (see FIG. 30). This essentially occurs continuously, wherein at the same time the first diaphragm device $7_1$ is completely open. However, as soon as the value of the rotation angle $\phi$ exceeds the 90° mark relative to the first focus $10_1$, the first diaphragm device $7_1$ completely, abruptly masks the first ray beam $8_1$ from the border regions towards the central region of the first ray beam $8_1$ while, given a continuing rotation, the value of the fan angle $\theta$ of the second ray beam $8_2$ is further reduced (see FIG. 31) until finally the second ray beam $8_2$ is also completely masked upon exceeding a value of the rotation angle $\phi$ of $90°+\theta/2$. This is shown in FIG. 32 for a rotation angle $\phi$ with a value of 135°.

According to the method above, the x-ray source 4 (not explicitly shown) causing the first ray beam $8_1$ is de facto activated first, and then the first ray beam $8_1$ is blended in at the start of a 90° scan. At the end of the 90° scan the first ray beam is masked out abruptly. The masking can ensue with the first diaphragm device $7_1$ or by a deactivation of the associated x-ray source 4. It can also proceed similarly with regard to the second ray beam $8_2$. The abrupt blending can ensue by an activation of the associated x-ray source 4 beforehand and a complete opening of the second diaphragm device $7_2$ ensuing suddenly at the correct point in time. The abrupt blending, however, alternatively can be realized by a completely open second diaphragm device $7_2$ and an activation of the associated x-ray source 4 (not explicitly shown) ensuing at the correct point in time. Toward the end of the 90° scan, the second diaphragm device $7_2$ then continuously masks the second ray beam $8_2$.

Figure 33:
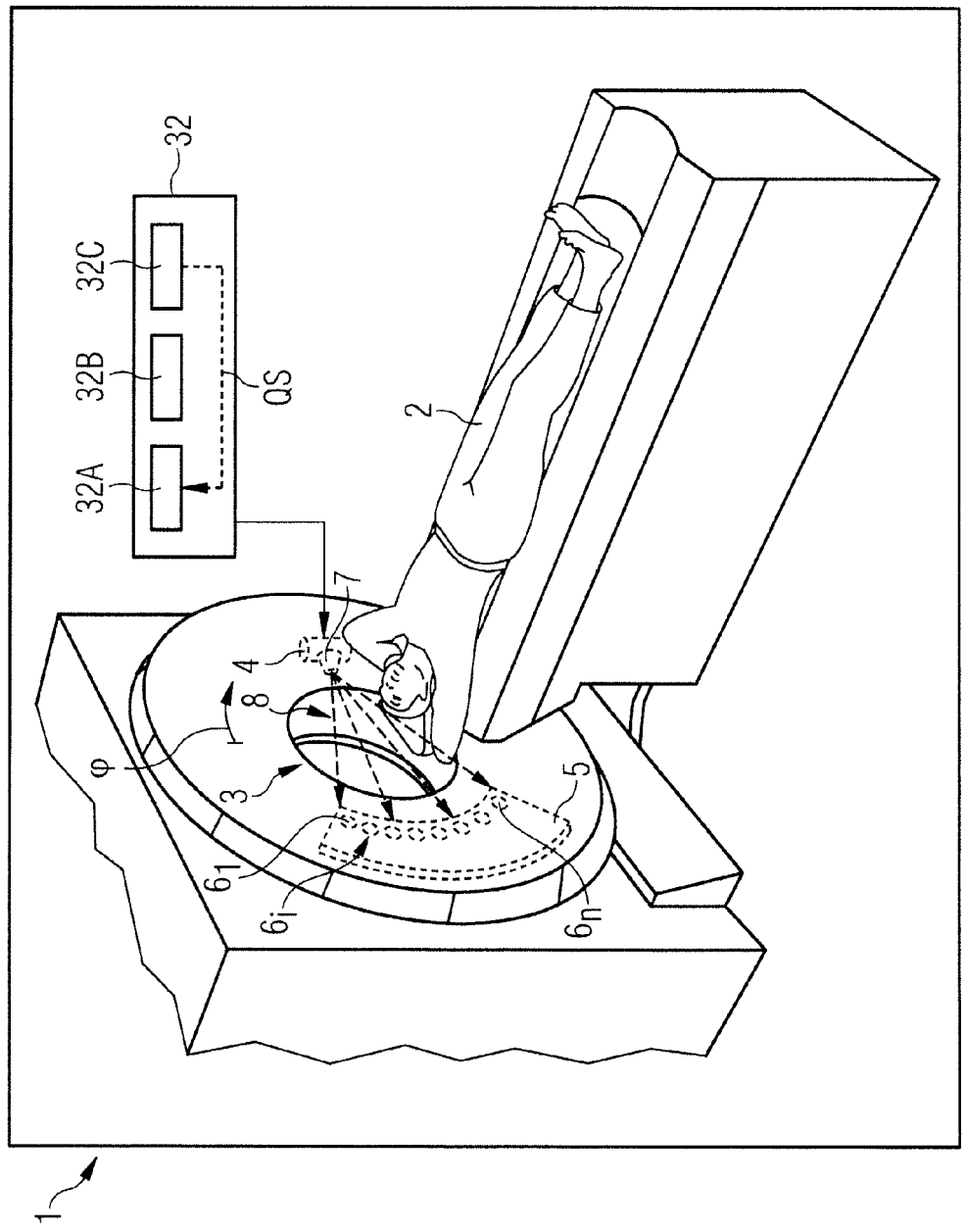
FIG. 33 shows an exemplary embodiment of a CT device according to the invention.

In the present case, the control device 32 is additionally fashioned to also control (depending on a rotation angle) the fan angle θ for accurately timed activation and deactivation of the respective x-ray tube 4 according to the description above. In FIG. 33 this is indicated by a source control signal QS that can be output by the diaphragm control module 32C to the x-ray source control module 32A.

In each case it can be advantageous if the final expansion of the focus 10 or, respectively, 10₁ and 10₂ is taken into account in the increase or, respectively, in the decrease of the fan angle θ (thus in the control of the respective diaphragm device 7 and 7₁ and 7₂), such that the channels 6ᵢ that are not masked out are exposed by the entire focus 10 and 10₁ and 10₂.

As stated above, the value of the fan angle θ preferably is varied with the use of a movable diaphragm situated at the tube (for example integrated into the tube 4). However, this can also be achieved by an additional diaphragm (not shown in detail) placed between the tube 4 and a measurement field edge, which additional diaphragm is rotated with the tube 4. The measurement field edge is, for example, defined by the inner area of the examination space 3.

Figure 3:
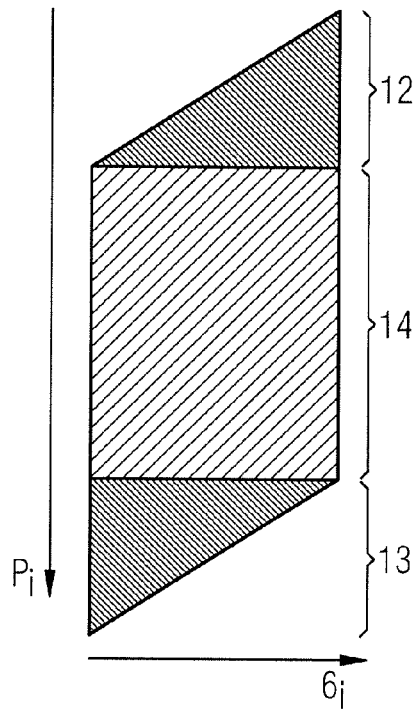
FIG. 3 is a sinogram for a single source CT device according to FIG. 1.

In the exemplary embodiments described in the preceding it is advantageously achieved that the sinogram of the CT device 1 exhibits none of the triangular regions 12 and 13 shown in FIG. 3 and FIG. 23, and therefore the unnecessarily applied dose associated with these triangular regions 12 and 13 is completely avoided.

In conclusion, it is noted again that the method described in detail in the preceding or, respectively, the device are merely exemplary embodiments which can be modified by those skilled in the art without departing from the scope of the invention. The invention was explained primarily using an application in a medically utilized CT device 1 and can also be applied in this context for apparatuses similar to CT apparatuses, for example angiography apparatuses with spatial data acquisition. The invention, however, is not limited to such applications. It can also be used in scientific and/or industrial applications. The described measures are usable both in sequence scans (for example in the 90° scan or the 180° scan with stationary examination subject) and in what are known as helix scans in which the examination subject 2 moves transversal to the fan-shaped ray beam 8 during the data acquisition.

As will be apparent to those skilled in the art, the exemplary embodiments described above can also be applied to situations in which more than two (for example three, four or five etc.) x-ray sources are used.

Although modifications and changes may be suggested by those skilled in the art, it is the intention of the inventor to embody within the patent warranted hereon all changes and modifications as reasonably and properly come within the scope of his contribution to the art.

I claim as my invention:

1. A radioscopic method to generate projections of the interior of an examination subject, comprising the steps of:
   placing an examination subject in an examination space of an imaging apparatus comprising at least one source of penetrating radiation that emits a ray beam of penetrating radiation having a fan angle;
   rotating said at least one penetrating radiation source, and thus also rotating the ray beam emitted therefrom, in a rotation plane containing said fan angle, in a rotation direction around the examination subject in the examination space;
   during a portion of rotation of said at least one penetrating radiation and said ray beam, varying the fan angle of said ray beam through a predetermined rotation angle that proceeds in succession through an initial rotation angle range and an end rotation angle range, and increasing a value of the fan angle from a start value to an end value in said initial rotation angle range, and reducing the value of the fan angle from said end value to said start value in said end rotation angle range; and
   detecting the penetrating radiation of the ray beam, attenuated by the examination subject and generating a projection data set from the detected attenuated penetrating radiation for each of a plurality of respective angular positions of the at least one x-ray source around the examination subject, and making said projection data sets available as an output from said detector in a form allowing reconstruction of an image of the examination subject therefrom.

2. A method as claimed in claim 1 wherein said ray beam has a first border region situated opposite to said rotation direction and a second border region situated in said rotation direction, and comprising increasing said value of said fan angle by adding penetrating radiation to said ray beam from said first border region toward said second border region, and decreasing the value of the fan angle by masking penetrating radiation in said ray beam from said first border region toward said second border region.

3. A method as claimed in claim 1 wherein said ray beam comprises a central region and first and second border regions respectively on opposite sides of said central region, said first border region being situated in said rotation direction and said second border region being situated opposite to said rotation direction, and comprising increasing the value of the fan angle by adding penetrating radiation in said ray beam from said central region toward each of said first and second border regions, and decreasing the value of the fan angle by masking penetrating radiation in said ray beam from each of said first and second border regions toward said central region.

4. A method as claimed in claim 1 comprising varying said fan angle through a plurality of discrete steps.

5. A method as claimed in claim 1 comprising varying said fan angle continuously without discrete steps.

6. A penetrating radiation imaging apparatus comprising:
   at least one penetrating radiation source;
   a rotatable gantry on which said at least one penetrating radiation source mounted, said gantry being operable to rotate said at least one penetrating radiation source around an examination space within said gantry in a rotation plane in a rotation direction;
   said at least one penetrating radiation sources emitting a ray beam of penetrating radiation directed toward said examination space and exhibiting a fan angle in said rotation plane comprising an initial range and an end range;
   a radiation detector system situated to detect the penetrating radiation from each ray beam;
   an adjustable diaphragm device mounted relative to said at least one penetrating radiation source to respectively delimit and change the fan angle of the ray beam emitted by the penetrating radiation source associated therewith during rotation of said at least one x-ray source, each diaphragm device comprising a diaphragm having a diaphragm aperture;
   a control device connected to said diaphragm device, said control device being configured to operate said diaphragm device to vary the fan angle of said ray beam during a portion of rotation of said gantry and said at least one penetrating radiation source around said examination space by changing the diaphragm aperture thereof; and
   said detector system generating a projection data set from said ray beam during rotation of said gantry and said at least one penetrating radiation sources around said examination space for each of a plurality of respective angular positions of the at least one x-ray source around the examination subject, and making said plurality of projection data sets available at an output of the detector system in a form allowing reconstruction of an image therefrom.

7. A device as claimed in claim 6 wherein said diaphragm having said diaphragm aperture is a first diaphragm, and wherein said diaphragm aperture is dimensioned to define a maximum value of said fan angle, and wherein each diaphragm device comprises a second diaphragm dimensioned and supported to interact with said diaphragm aperture of said first diaphragm to change the value of the fan angle between said start value and said end value by operation of said control device.

8. A device as claimed in claim 7 wherein said second diaphragm comprises a movable slit diaphragm having a diaphragm slit therein proceeding transverse to a movement direction of said movable slit diaphragm.

9. A device as claimed in claim 8 wherein said movable slit diaphragm is movable passed said first diaphragm.

10. A device as claimed in claim 8 wherein said movable slit diaphragm comprises an actuation stage that moves said movable slit diaphragm parallel to said first diaphragm.

11. A device as claimed in claim 7 wherein said second diaphragm is comprised of two movable plates that are movable relative to each other to form a second diaphragm aperture therebetween.

12. A device as claimed in claim 11 comprising two actuators that respectively move said movable plates to change said aperture of said second diaphragm.

13. A device as claimed in claim 6 wherein said detector system comprises a plurality of discrete detectors equal in number to said plurality of diaphragm devices, each discrete detector being located opposite one of said diaphragm devices on said gantry with the examination space therebetween, and wherein said gantry rotates said discrete detectors together with said penetrating radiation sources around said examination space, each of said discrete detectors having an active detector region dimensioned to cause the fan angle of the ray beam incident thereon to completely expose said active region, as viewed in a circumferential direction around said examination space.

* * * * *